(12) United States Patent
Boatman et al.

(10) Patent No.: US 7,722,795 B2
(45) Date of Patent: May 25, 2010

(54) MEDICAL DEVICE INCLUDING UNITARY, CONTINUOUS PORTION OF VARYING DUROMETER

(75) Inventors: Scott E. Boatman, Bloomington, IN (US); David G. Burton, Bloomington, IN (US); Michael C. Hoffa, Bloomington, IN (US); Thomas A. Osborne, Bloomington, IN (US); David A. Drewes, Jr., Bloomington, IN (US); David R. Lessard, Bloomington, IN (US); Maggie A. Z. Hupcey, Indianapolis, IN (US)

(73) Assignee: Cook Incorporated and Sabin Corporation, Bloomington, IN (US)

( * ) Notice: Subject to any disclaimer, the term of this patent is extended or adjusted under 35 U.S.C. 154(b) by 1589 days.

(21) Appl. No.: 10/813,415

(22) Filed: Mar. 30, 2004

(65) Prior Publication Data

US 2006/0016064 A1 Jan. 26, 2006

Related U.S. Application Data

(62) Division of application No. 09/848,742, filed on May 3, 2001, now Pat. No. 6,881,209.

(60) Provisional application No. 60/207,058, filed on May 25, 2000.

(51) Int. Cl.
*B29C 35/08* (2006.01)
(52) U.S. Cl. ...................... 264/494; 604/525
(58) Field of Classification Search .............. 264/494; 604/525
See application file for complete search history.

(56) References Cited

U.S. PATENT DOCUMENTS 3,904,519 A 9/1975 McKinney, Jr. et al.

(Continued)

FOREIGN PATENT DOCUMENTS

EP 0872258 10/1998

(Continued)

OTHER PUBLICATIONS

Technical Information; Pebax Resins, 33 Series Property Comparison.

(Continued)

*Primary Examiner*—Christina Johnson
*Assistant Examiner*—Galen Hauth
(74) *Attorney, Agent, or Firm*—Brinks Hofer Gilson & Lione

(57) ABSTRACT

A medical device (110) including a catheter shaft (111) and a unitarily and continuously formed portion (108) having a varying durometer, and optionally including an expandable balloon (18, 118). One or both of the unitarily and continuously formed portion (108) and the balloon (18, 118) are made from an irradiation cross-linked or cross-linkable mixture of a polyamide elastomer and at least one additional cross-linking reactant. The polyamide elastomer can be a polyester amide, a polyether ester amide or a polyether amide, and is preferably a nylon block copolymer. The aromatic molecule can be 1,3,5 triethyl benzene; 1,2,4 triethyl benzene; and 1,3,5 triisopropyl benzene. The cross-linking reactant can be: (a) a difunctional material, (b) a trifunctional material, (c) a tetrafunctional material, or (d) an aromatic molecule containing at least two ring substituents, each of the ring substituents having labile hydrogens at a benzylic site therein. The cross-linking reactant can also be diallyl phthalate or meta-phenylene dimaleimide.

3 Claims, 5 Drawing Sheets

U.S. PATENT DOCUMENTS

| | | | |
|---|---|---|---|
| 4,154,244 A | 5/1979 | Becker et al. | |
| 4,156,538 A * | 5/1979 | Roberts | 281/29 |
| 4,172,859 A | 10/1979 | Epstein | |
| 4,191,231 A | 3/1980 | Winchell et al. | |
| 4,212,965 A | 7/1980 | Campbell | |
| 4,276,250 A | 6/1981 | Satchell et al. | |
| 4,290,428 A | 9/1981 | Durand et al. | |
| 4,385,635 A | 5/1983 | Ruiz | |
| 4,436,887 A * | 3/1984 | Chromecek et al. | 526/263 |
| 4,444,816 A | 4/1984 | Richards et al. | |
| 4,490,421 A | 12/1984 | Levy | |
| 4,563,181 A | 1/1986 | Wijayarathna et al. | |
| 4,617,355 A | 10/1986 | Gabbert et al. | |
| 4,636,346 A | 1/1987 | Gold et al. | |
| 4,657,024 A | 4/1987 | Coneys | |
| 4,665,557 A | 5/1987 | Kamp | |
| 4,739,768 A | 4/1988 | Engelson | |
| 4,753,980 A | 6/1988 | Deyrup | |
| 4,775,371 A | 10/1988 | Mueller, Jr. | |
| 4,861,830 A | 8/1989 | Ward, Jr. | |
| 4,898,591 A | 2/1990 | Jang et al. | |
| 4,906,244 A | 3/1990 | Pinchuk et al. | |
| 4,938,676 A | 7/1990 | Jackowski et al. | |
| 4,950,239 A | 8/1990 | Gahara et al. | |
| 4,963,313 A | 10/1990 | Noddin et al. | |
| 4,964,409 A | 10/1990 | Tremulis | |
| 5,017,259 A | 5/1991 | Kohsai | |
| 5,017,325 A | 5/1991 | Jackowski et al. | |
| 5,036,118 A | 7/1991 | Martinez | |
| 5,045,072 A | 9/1991 | Castillo et al. | |
| 5,049,109 A | 9/1991 | Radovic et al. | |
| 5,085,649 A | 2/1992 | Flynn | |
| 5,088,991 A * | 2/1992 | Weldon | 604/523 |
| 5,147,332 A | 9/1992 | Moorehead | |
| 5,180,376 A | 1/1993 | Fischell | |
| 5,208,269 A | 5/1993 | Brown | |
| 5,221,270 A | 6/1993 | Parker | |
| 5,222,949 A * | 6/1993 | Kaldany | 604/524 |
| 5,234,416 A * | 8/1993 | Macaulay et al. | 604/527 |
| 5,246,705 A | 9/1993 | Venkatraman et al. | |
| 5,258,160 A | 11/1993 | Utsumi et al. | |
| 5,264,260 A | 11/1993 | Saab | |
| 5,270,086 A | 12/1993 | Hamlin | |
| 5,295,962 A | 3/1994 | Crocker et al. | |
| 5,300,048 A | 4/1994 | Drewes, Jr. et al. | |
| 5,304,340 A | 4/1994 | Downey | |
| 5,306,246 A | 4/1994 | Sahatjian et al. | |
| 5,310,779 A * | 5/1994 | Lai | 524/588 |
| 5,318,587 A | 6/1994 | Davey | |
| 5,328,468 A | 7/1994 | Kaneko et al. | |
| 5,330,428 A | 7/1994 | Wang et al. | |
| 5,338,296 A | 8/1994 | Dalessandro et al. | |
| 5,342,299 A | 8/1994 | Snoke et al. | |
| 5,342,386 A | 8/1994 | Trotta | |
| 5,344,401 A | 9/1994 | Radisch et al. | |
| 5,368,564 A | 11/1994 | Savage | |
| 5,380,304 A | 1/1995 | Parker | |
| 5,385,173 A | 1/1995 | Garglulo | |
| 5,399,164 A | 3/1995 | Snoke et al. | |
| 5,423,764 A | 6/1995 | Fry | |
| 5,423,838 A | 6/1995 | Willard | |
| 5,433,713 A | 7/1995 | Trotta | |
| 5,451,747 A | 9/1995 | Sullivan et al. | |
| 5,454,795 A | 10/1995 | Samson | |
| 5,456,674 A | 10/1995 | Bos et al. | |
| 5,496,294 A | 3/1996 | Hergenrother et al. | |
| 5,498,250 A | 3/1996 | Prather | |
| 5,499,975 A | 3/1996 | Cope et al. | |
| 5,507,725 A | 4/1996 | Savage et al. | |
| 5,522,961 A | 6/1996 | Leonhardt | |
| 5,531,715 A | 7/1996 | Engelson et al. | |
| 5,533,985 A | 7/1996 | Wang | |
| 5,542,925 A | 8/1996 | Orth | |
| 5,542,937 A | 8/1996 | Chee et al. | |
| 5,545,133 A | 8/1996 | Burns et al. | |
| 5,554,120 A | 9/1996 | Chen et al. | |
| 5,554,121 A | 9/1996 | Ainsworth et al. | |
| 5,554,139 A | 9/1996 | Okajima | |
| 5,556,383 A | 9/1996 | Wang et al. | |
| 5,565,523 A | 10/1996 | Chen et al. | |
| 5,569,218 A | 10/1996 | Berg | |
| 5,584,821 A | 12/1996 | Hobbs et al. | |
| 5,599,291 A | 2/1997 | Balbierz et al. | |
| 5,599,305 A | 2/1997 | Hermann et al. | |
| 5,599,325 A | 2/1997 | Ju et al. | |
| 5,620,649 A | 4/1997 | Trotta | |
| 5,622,665 A | 4/1997 | Wang | |
| 5,649,906 A | 7/1997 | Gory et al. | |
| 5,649,909 A | 7/1997 | Cornelius | |
| 5,671,780 A | 9/1997 | Kertesz | |
| 5,695,482 A | 12/1997 | Kaldany | |
| RE35,717 E | 1/1998 | Nahm | |
| 5,707,332 A | 1/1998 | Weinberger | |
| 5,714,110 A | 2/1998 | Wang et al. | |
| 5,728,063 A | 3/1998 | Preissman et al. | |
| 5,755,690 A | 5/1998 | Saab | |
| 5,769,817 A | 6/1998 | Burgmeier | |
| 5,769,830 A | 6/1998 | Parker | |
| 5,772,641 A | 6/1998 | Wilson | |
| 5,792,105 A | 8/1998 | Lin et al. | |
| 5,792,124 A | 8/1998 | Horrigan et al. | |
| 5,795,325 A | 8/1998 | Valley et al. | |
| 5,797,877 A | 8/1998 | Hamilton et al. | |
| 5,807,520 A * | 9/1998 | Wang et al. | 264/520 |
| 5,814,061 A | 9/1998 | Osborne et al. | |
| 5,826,588 A | 10/1998 | Forman | |
| 5,833,657 A | 11/1998 | Reinhardt et al. | |
| 5,836,925 A | 11/1998 | Soltesz | |
| 5,879,499 A | 3/1999 | Corvi | |
| 5,891,110 A | 4/1999 | Larson et al. | |
| 5,900,444 A | 5/1999 | Zamore | |
| 5,906,605 A | 5/1999 | Coxum | |
| 5,908,413 A | 6/1999 | Lange et al. | |
| 5,911,715 A | 6/1999 | Berg et al. | |
| 5,913,857 A | 6/1999 | Ritchart et al. | |
| 5,919,570 A | 7/1999 | Hostettler et al. | |
| 5,921,915 A | 7/1999 | Aznoian et al. | |
| 5,947,940 A | 9/1999 | Beisel | |
| 5,948,489 A | 9/1999 | Hopkins | |
| 5,951,494 A | 9/1999 | Wang et al. | |
| 5,951,929 A | 9/1999 | Wilson | |
| 5,951,941 A | 9/1999 | Wang et al. | |
| 5,961,532 A | 10/1999 | Finley et al. | |
| 5,992,000 A | 11/1999 | Humphrey et al. | |
| 5,993,415 A | 11/1999 | O'Neil et al. | |
| 5,998,551 A * | 12/1999 | O'Neil et al. | 525/426 |
| 6,036,682 A | 3/2000 | Lange et al. | |
| 6,042,588 A | 3/2000 | Munsinger et al. | |
| 6,048,485 A | 4/2000 | Field et al. | |
| 6,050,949 A | 4/2000 | White et al. | |
| RE36,717 E | 5/2000 | Thompson | |
| 6,165,165 A | 12/2000 | Cecchi et al. | |
| 6,595,654 B2 * | 7/2003 | Washburn | 362/130 |
| 6,596,818 B1 | 7/2003 | Zamore | |

FOREIGN PATENT DOCUMENTS

| | | |
|---|---|---|
| EP | 0934755 | 8/1999 |
| WO | WO 9617883 | 6/1996 |
| WO | WO 9725093 | 7/1997 |
| WO | WO 9815199 | 4/1998 |
| WO | WO 9855171 | 12/1998 |
| WO | WO 9915078 | 4/1999 |

| WO | WO 9929353 | 6/1999 |
| WO | WO 9934855 | 7/1999 |
| WO | WO 9936119 | 7/1999 |
| WO | WO 9948548 | 9/1999 |
| WO | WO 0119425 | 3/2001 |

OTHER PUBLICATIONS

Joseph R. Flesher, Jr.; Modern Plastics *Polyether block amide: high-performance TPE*; Sep. 1987, vol. 64, No. Nine, four pages starting on p. 100.

* cited by examiner

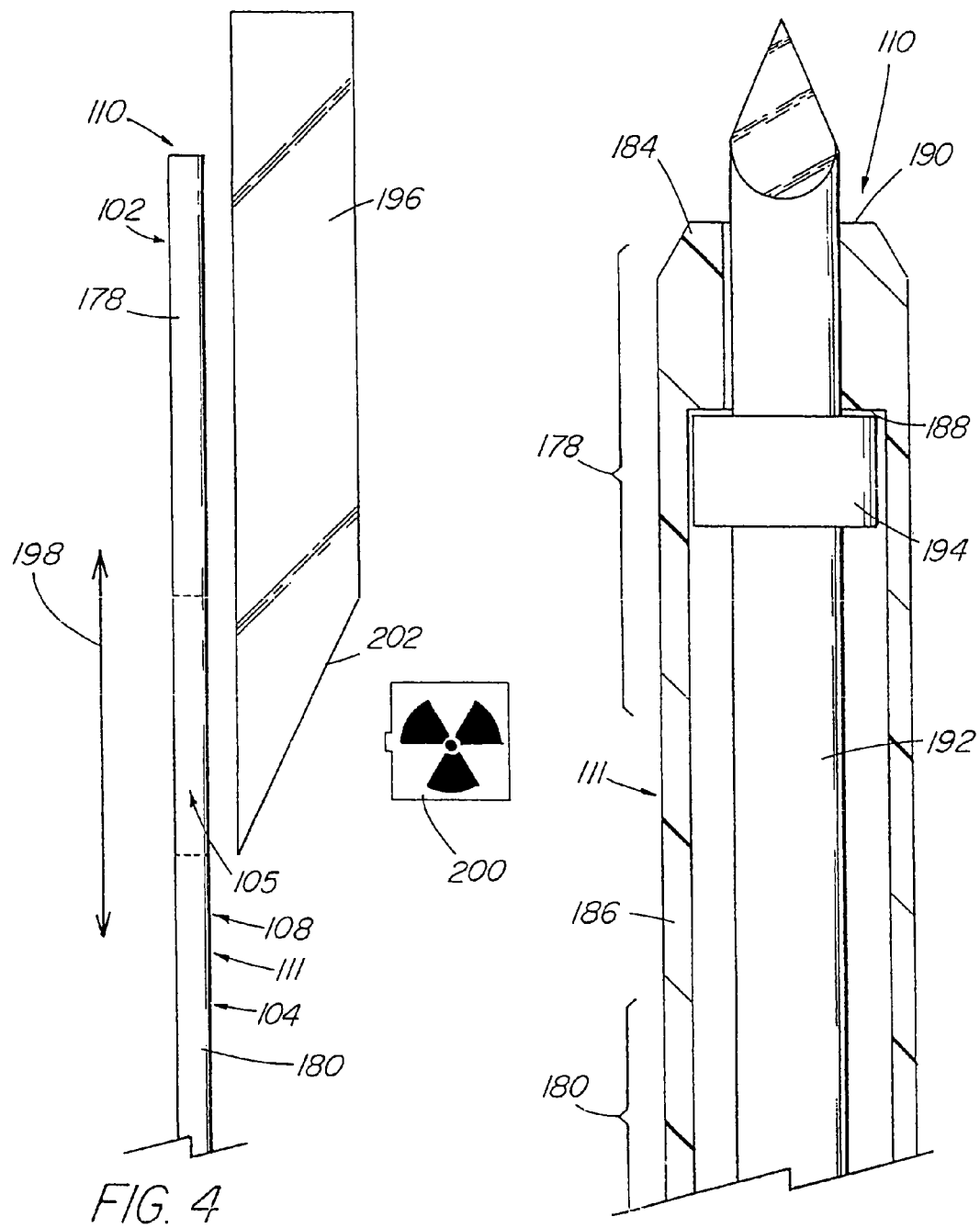

MEDICAL DEVICE INCLUDING UNITARY, CONTINUOUS PORTION OF VARYING DUROMETER

CROSS-REFERENCE TO RELATED APPLICATIONS

This is a Divisional Patent Application of patent application Ser. No. 09/848,742, filed May 3, 2001, now U.S. Pat. No. 6,881,209 which is based on patent application Ser. No. 09/663,747, filed Sep. 15, 2000 and also claims priority of U.S. Provisional Patent Application Ser. No. 60/207,058 filed May 25, 2000.

FIELD OF THE INVENTION

This invention relates generally to medical devices such as devices for deploying another medical device such as a stent into a patient; or devices which are themselves to be introduced into a patient, for example, for establishing a passage or lumen in a patient, for expanding a narrowed or obstructed passage or lumen in a patient or for introducing a therapeutic or diagnostic fluid into a patient.

BACKGROUND OF THE INVENTION

Medical devices which incorporate inflatable or expandable balloons serve a wide variety of purposes. The balloon is carried on or affixed to a catheter shaft for delivery of the balloon to a desired location in the patient. The catheter shaft includes a lumen for introducing an inflation fluid into the balloon. For example, such catheter balloons are widely known to be useful for performing angioplasty procedures or the like, in which narrowings or obstructions in blood vessels or other body passageways are altered in order to increase blood flow through the narrow or obstructed area. More specifically, in a typical balloon angioplasty procedure, a balloon catheter is percutaneously introduced into the patient by way of the arterial system and advanced until the balloon of the catheter lies across the vascular narrowing or obstruction. The balloon is then inflated to dilate the vessel lumen at the site of the narrowing or obstruction. If desired, a stent may be positioned over the balloon and deployed at the site of the narrowing or obstruction to ensure that the dilated vessel lumen remains open. Balloon catheters find utility in a wide range of procedures, including valvuloplasty and urological procedures, among others.

The balloons of prior balloon catheters have been constructed from a wide variety of polymeric materials. These balloons each have their own advantages and drawbacks. Balloons comprising polyethylene terephthalate (PET), for example, have a relatively low degree of distention or expansion once they are inflated. This generally minimizes any potential adverse effects from overinflation or overexpansion of the balloon or any stent carried on it. Semi-distending or non-distending balloons often possess relatively high tensile strength, burst pressure and puncture resistance, qualities highly desirable for dilating tough lesions or for deploying and expanding stents carried over them.

However, body vessels such as arteries are generally tapered, and the locations at which narrowings or obstructions may occur vary, so that a balloon which closely matches the ultimately desired diameter of the vessel may not be readily available. Moreover, it may at times be desirable to be able to increase the diameter of the balloon beyond that which had been contemplated before the balloon procedure was begun. While balloons comprising materials such as polyvinyl chloride can be more distensible than PET or the like, balloons comprising such materials often possess a significantly lower tensile strength, burst pressure or puncture resistance than the less-distensible balloons. Overinflation of such balloons is also possible.

A variety of attempts have been made to construct medical device balloons from materials which yield balloons of good strength (that is, relatively high tensile strength and burst pressure, and good puncture resistance) while retaining an adequate degree of compliance, that is, an acceptable ratio of balloon diameter growth under an applied pressure to that balloon pressure. Each of these attempts possesses its own advantages and disadvantages. Balloons made from materials such as PET may possess excessive crystallinity or may be too stiff, so that such balloons may be resistant to the folding desired to minimize the profile of the catheter in which the balloon is employed; such resistance to folding is particularly problematic when the balloon is deflated following inflation during an in situ application, in order to be retracted into the distal end of the catheter for withdrawal. A minimal catheter profile is a highly desirable characteristic of balloon catheters, however. Some materials do not readily accept coating with drugs or lubricants, and some materials are difficult to fuse or adhere to conventional catheter shafts. Balloons made of some biaxially oriented nylons or polyamides have been asserted to overcome some of these problems.

Catheter balloons comprised of block copolymers have been suggested as a way of achieving an acceptable combination of balloon strength and elasticity. For example, it is known that catheter balloons can be constructed from polyamide/polyether block copolymers, commonly identified by the acronym PEBA (polyether block amide). Many of such copolymers can be characterized by a two phase structure, one being a thermoplastic region that is primarily a polyamide, semicrystalline at room temperature, and the other being an elastomer region that is rich in polyether. Balloons comprising such copolymers are asserted to possess a desirable combination of strength, compliance and softness. Catheter balloons comprising blends of two or more such copolymers are also known, and it has been asserted that irradiating such blends can enhance the properties of the resulting balloons, including increased burst pressures.

It would be highly advantageous to have medical devices which included expandable or inflatable balloons with improved strength, for example, with greater tensile strength, burst pressure and/or puncture resistance, while simultaneously possessing acceptable compliance (in this case, an acceptable ratio of balloon diameter growth to balloon pressure). It would also be highly advantageous to have medical devices made from materials which meet a variety of desirable processing criteria, including thermal stability, non-toxicity, non-volatility, high boiling point (preferably, solid at room temperature), high flash point, insensitivity to moisture and commercial availability.

It would also be advantageous to have balloon-type or other medical devices (such as catheters) which had a varying durometer or durometer hardness, that is, a varying resistance to deformation upon the application of a transverse force, but which did not need to be constructed from multiple pieces of different durometers. "Durometer" or "durometer hardness" usually refers to the resistance of materials such as rubber or plastics to deformation, typically to deformation by an indenter of specific size and shape under a known load. The stiffness or resistance to lateral deformation of an elongate rubber, plastic or portion of a medical device often correlates to durometer hardness, as does balloon burst pressure. The stiffness or resistance to lateral deformation of such an elongate portion also often correlates to the modulus of elasticity or flexural modulus of the rubber, plastic or other material of which the elongate portion is made. For brevity, the use of the phrase "varying durometer" herein refers to changes in any or all of durometer hardness, stiffness, resistance to lateral deformation, modulus of elasticity, flexural modulus or other desirable functional property. Use of the word "durometer" herein is therefore not limited to durometer hardness or to properties which correlate to durometer hardness. As used herein, "durometer" instead also includes properties such as modulus of elasticity and flexural modulus which do not necessarily correlate to durometer hardness, since materials having the same durometer hardness may have different moduli of elasticity or different flexural moduli, and thus different stiffnesses.

Varying durometer along the length of a medical device enables different parts of a device to perform different functions. Unfortunately, present methods or structures for achieving a variable durometer along the length of a catheter shaft or other medical device entail securing two or more separate pieces of different durometer by adhesion, heat bonding, butt bonding, sonic welding, mechanical means or the like. The resulting structures have a very rapid or abrupt change in composition, and therefore a very rapid or abrupt change in durometer, at the junction of the pieces of different durometer. One drawback of such structures is that the very rapid or abrupt change in durometer creates a kink point at which the catheter shaft or the like is subject to folding over during use, making the catheter shaft or the like more difficult to advance in the patient. Eliminating this abrupt change in composition while allowing the medical device (or portion thereof) to have different durometers along its length would make it easier to advance a catheter shaft or the like in a patient. Moreover, particularly in devices having very small cross-sectional diameters, it is often difficult to reliably secure together different pieces of very small diameter. This difficulty would be avoided if the different pieces of the medical devices could be continuously formed. It would further be advantageous to achieve a varying durometer without the need for heat bonding two or more separate pieces, as heat bonding the pieces adds heat history to them, along with an associated risk of degradation at the bond site. It would also be advantageous to have medical devices in which a change in durometer was gradual over an appreciable length of the devices, that is, over a length long enough to improve the practical utility of such devices, such as by obviating kinking or the like.

BRIEF SUMMARY OF THE INVENTION

Many of the foregoing problems are solved and a technical advance is achieved in an illustrative medical device for positioning an included balloon within a human or veterinary patient, for example, for deploying another medical device such as a stent in the patient or for expanding a passage or lumen in the patient. More particularly, in a first preferred embodiment, the medical device of the present invention comprises a catheter shaft and an expandable balloon carried by the catheter shaft. The medical device of the present invention is characterized in that the balloon comprises an irradiation cross-linked mixture of a polyamide elastomer and at least one additional cross-linking reactant.

This additional cross-linking reactant performs a role which is quite different from that performed by the two reaction promoters disclosed in International Application WO 98/55171. That Application is directed to a cross-linked nylon block copolymer which comprises an irradiation cross-linked copolymer containing a polyamide block and an elastomeric block, including a compound which promotes cross-linking therein. The process disclosed in that application comprises supplying the nylon block copolymer with a cross-linking "promotoer" (sic.) and exposing the block copolymer to irradiation sufficient to cross-link the copolymer. Only two promoters are disclosed, triallylcyanurate and triallylisocyanurate, at 2 percent by weight in PEBAX® brand nylon block copolymer (Atochem, Inc., brand of polymers consisting of polyether blocks separated by polyamide blocks). Irradiation is carried out at 5 to 20 megarads (no specific type of irradiation is disclosed), although the Application points out that degradation of the material may take place when total irradiation becomes too high, for example, at 15 or 20 megarads. That Application claims (among others) an improvement in a balloon type catheter having a tubular shaft comprising a nylon block copolymer and an integrally formed balloon section, the improvement comprising irradiation crosslinking the copolymer of the balloon section, wherein the crosslinking lowers the percent elongation of the balloon section as compared to the elongation prior to crosslinking. The only apparent support in the specification for that claim appears to be a single statement that, in the case of balloon catheters manufactured from a nylon block copolymer, the invention therein provides for the preparation of a balloon type catheter wherein the balloon section relative to the shaft can be converted into a thermoset or crosslinked type structure, thereby increasing its overall mechanical strength, performance, and durability. That Application appears to make no other disclosure of any process whatsoever for manufacturing such a balloon, and appears to contain absolutely no details as to how such a process could or should be carried out.

The present invention is quite distinct; the cross-linking reactant of the present invention and the promoter of that Application appear to act in different ways to perform different functions. "Promoter" is a well-recognized term of art, of course, referring to a material which enhances the activity of a catalyst. More particularly, a promoter is a substance that, when added in relatively small quantities to a catalyst, increases its activity; Lewis, Sr., Hawley's Condensed Chemical Dictionary 12th (Van Nostrand Reinhold Company, New York, N.Y., 1993) (definition 1), at 966; or is a chemical which itself is a feeble catalyst, but greatly increases the activity of a given catalyst; Parker, McGraw-Hill Dictionary of Scientific and Technical Terms 5th (McGraw-Hill, Inc., New York, N.Y., 1994) (first definition), at 1589. Catalysts, of course, accelerate or retard the velocity of a chemical reaction without being consumed during the course of those reactions. They do not become incorporated into the chemical structures of the products of the reactions, and in theory can be recovered at the end of the reaction essentially unaltered in form and amount (even though in practice they might be retained in the physical object constituted by the reaction products). This is presumably true of the two materials mentioned in that Application, since they appear to be solely described in that Application as "promoters." While it might be argued whether energy should properly be called a catalyst, it is believed that the use of the word "promoters" in that Application would be readily understood by those in the medical device field to refer to materials which increased the activity of the irradiation employed in that Application, that is, increased irradiation cross-linking between the chains themselves of the nylon block copolymer it discloses.

In direct contrast to any balloon or medical device containing the two specific promoters of that Application at their disclosed concentrations, the medical device of the present invention comprises a balloon in which one or more specific cross-linking reactants are, by irradiation, chemically incorporated into the polyamide elastomer with which they are initially mixed. Thus, where the two promoters of that Application would cause the various chains within the polyamide elastomer of any balloon to cross-link directly to one another, the specific cross-linking reactants in the balloon of the present invention instead themselves form and constitute links or bridges between the various chains within the polyamide elastomer. Thus, the molecular structure and physical properties of the balloon incorporated in the medical device of the present invention are different from those which might be expected to be possessed by a balloon which included either of the two catalysts or promoters of that Application.

The particular cross-linking reactants useful in the medical device of the present invention, and in particular, in the balloon thereof, are expected to include difunctional materials such as diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether. Useful cross-linking reactants are also expected to include trifunctional materials such as 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; and tetrafunctional materials such as tetraallyl cis,cis,cis,cis-cyclopentane-1,2,3,4-tetracarboxylate; and N,N,N',N'-tetraallylethylenediamine. Useful materials are also expected to include aromatic molecules containing at least two ring substituents, each of the ring substituents having labile hydrogens at a benzylic site therein. 1,3,5 triethyl benzene; 1,2,4 triethyl benzene; and 1,3,5 tri-isopropyl benzene are commercially available examples of such aromatic molecules containing at least two substituents having labile hydrogens at a benzylic site. Useful materials are further expected to include diallyl phthalate and meta-phenylene dimaleimide; these latter two constitute a second preferred embodiment of the present invention.

All of these materials are expected to possess at least several of a variety of desirable characteristics for manufacturing the medical device of the present invention: thermal stability, non-toxicity, non-volatility, high boiling point (preferably, solid at room temperature), high flash point, insensitivity to moisture and commercial availability. However, not all of these materials possess all of these desirable characteristics. Other materials capable of forming allylic or benzylic radicals having comparable reactivity should be useful as well. The primary criteria for selecting such other materials may be that they are less reactive than species such as epoxies, methacrylates and acrylates; and that they are relatively "small" molecules, that is, they are small enough to fit between (and thereby be capable of cross-linking) the various chains of the particular polyamide elastomer being used. The materials must of course be multifunctional, to be able to cross-link to at least two of those chains.

The more reactive species such as epoxies, methacrylates and acrylates are probably undesirable for use in the medical device of the present invention because they are likely to cross-link the polyamide elastomer too rapidly, completing the cross-linking reaction during preliminary thermal processing of the polyamide elastomer (prior to its being formed into the balloon of the device). Such premature cross-linking clogs the processing equipment, such that completion of the balloon-forming process is impossible. Multifunctional allylic materials are more stable and less reactive than these, so that they readily survive thermal processing but are still reactive enough when exposed to a source of energy to achieve good cross-linking.

The allylic radical and the benzylic radical differ in bond dissociation energies (and hence radical stabilities and reactivities) by only 2 kcal/mol (7 kJ/mol); J. March, Advanced Organic Chemistry 4th, at 191 (John Wiley & Sons, New York, N.Y., 1992). Accordingly, a wide variety of multifunctional benzylic small molecules are expected to be useful in the medical device of the present invention; the three listed above have the advantage of being commercially available at the present time. The selection of other materials having suitably positioned labile hydrogens should be well within the level of skill in the field of designing medical devices of this type, since the recognition of labile hydrogen positions is generally taught quite early in introductory (college sophomore) organic chemistry.

While some modest degree of trial-by-error experimentation may be needed to confirm the practical utility of any particular allylic or benzylic material contemplated for use in the present invention but not specifically disclosed herein, such experimentation is not believed to be undue under the circumstances, but is instead believed to be substantially below the amount of testing that would be required for regulatory approval for actually marketing a medical device incorporating a balloon comprising such a particular material as a cross-linking reactant.

While attempting to manufacture a medical device balloon employing the two promoters disclosed in International Application WO 98/55171, it was discovered that these two specific materials could in fact act as cross-linking reactants (instead of merely augmenting the cross-linking activity of the disclosed irradiation) under concentrations or conditions other than the concentrations or conditions disclosed in that Application. More particularly, attempts to make a parison for forming a medical device balloon from a mixture of PEBAX® brand nylon block copolymer with 2 percent by weight of one of those materials were generally unsuccessful or unacceptable for commercial purposes, due to the significant formation of gelling in the parison. "Gelling" is a term of art which indicates the formation of small, discrete volumes, areas, particles or particulates which are a result of premature, undesirable thermal cross-linking of the copolymer or other polyamide elastomer itself. "Gelling" also includes other defects arising during the manufacture of the copolymer or other polyamide elastomer. Gelling in the particular mixture under consideration prevented the successful use of the resulting parison to form a balloon for commercial purposes.

Since that Application teaches that higher levels of irradiation are undesirable, it is believed that those skilled in the field would have concluded that the only alternative left for improving the amount of cross-linking would have been to increase the amount of promoter mixed with the copolymer. Efforts in this direction were unsuccessful. Unexpectedly, it was found that an acceptable balloon could be obtained by lowering, not increasing, the amount of the promoter. As a result, gelling was decreased to an acceptable level. It was found that at these lower levels the so-called "promoter" itself acted as a cross-linking reactant, incorporated in the structure of the cross-linked copolymer between the chains of the copolymer. Such a result appears to be directly contrary to any reasonable expectation from the disclosure of that Application.

Accordingly, in a third preferred embodiment, the medical device of the present invention comprises a combination which is comparable to the first preferred embodiment, but which is instead characterized in that its balloon is formed from an irradiated mixture of a polyamide elastomer and no more than about 1.5 percent by weight of either triallyl cyanurate or triallyl isocyanurate. It is believed that these two materials advantageously possess most or all of the desirable characteristics mentioned above.

In all of these embodiments of the present invention, the polyamide elastomer can be one or more members of any of the three generally recognized families of polyamide elastomers: polyester amides (or PESAs), polyether ester amides (PEEAs) or polyether amides (PETAs). Representative PESAs include ESTAMID® brand polymer from Dow Chemical Company. Representative PEEAs include PEBAX® brand nylon block copolymer, VESTAMID® brand polymer from Creanova Corporation and GRILAMID®) brand polymer from Esmer Corporation. Representative PETAs include GRILON® brand polymer, also from Esmer Corporation.

Other preferred embodiments of the present invention described in more detail below include the processes by which these three embodiments of the medical device of the present invention are assembled. The medical device of the present invention may be particularly advantageous in that the puncture resistance, strength and burst pressure of its balloon may be improved with respect to comparable irradiation cross-linked balloons lacking any cross-linking reactant.

In a first aspect, then, the present invention is directed to a medical device comprising: a catheter shaft; and an expandable balloon carried by the catheter shaft; wherein the balloon comprises an irradiation cross-linked mixture of a polyamide elastomer and at least one additional cross-linking reactant, the cross-linking reactant comprising: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether; (b) a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis,cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein. In a second aspect, the present invention is directed to such a device in which the at least one additional cross-linking agent comprises diallyl phthalate or meta-phenylene dimaleimide.

The balloon of the medical device preferably comprises an amount of the cross-linking reactant sufficient to give the balloon a strength generally about equal to and perhaps in some cases greater than that of a balloon composed of the polyamide elastomer and comparably cross-linked by irradiation, but in the absence of any cross-linking reactant, agent or promoter. The balloon more preferably comprises about 1 to about 2 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material. The balloon alternatively comprises about 1 to about 2 percent by weight diallyl phthalate or meta-phenylene dimaleimide.

The balloon of the medical device further preferably comprises a mixture of the polyamide elastomer and the cross-linking reactant which has been cross-linked by irradiation with an electron beam or with ultraviolet, X- or gamma rays. More preferably, the balloon comprises a mixture of the polyamide elastomer and the cross-linking reactant which has been cross-linked by exposure to about 0.5 to about 20 megarads of radiation. It is preferred that the balloon is formed by inflation of the mixture of the polyamide elastomer and the cross-linking reactant after the mixture has been cross-linked by irradiation.

As indicated above, the balloon of the medical device can comprise any member of the polyamide elastomer families, such as polyester amides, polyether ester amides or polyether amides. The balloon preferably comprises a nylon block copolymer including polyamide blocks separated by elastomeric polyether blocks or segments. Suitable nylon block copolymers of this type are sold under the trademark PEBAX® by Atochem, Inc. Useful nylon block copolymers can instead include polyamide blocks separated by other elastomeric blocks or segments, such as polyesters, hydrocarbons or polysiloxanes.

When the balloon comprises an irradiation cross-linked mixture of a polyamide elastomer and an aromatic molecule, it is preferred that the aromatic molecule containing at least two ring substituents, each of the ring substituents having labile hydrogens at a benzylic site therein, is selected from the class consisting of 1,3,5 triethyl benzene; 1,2,4 triethyl benzene; and 1,3,5 triisopropyl benzene.

In a third aspect, the present invention is directed to a medical device comprising: a catheter shaft; and an expandable balloon carried by the catheter shaft; wherein the balloon comprises an irradiation cross-linked mixture of a polyamide elastomer and no more than about 1.5 percent by weight of at least one additional cross-linking reactant, the cross-linking reactant comprising triallyl cyanurate or triallyl isocyanurate. Preferably, the balloon comprises an amount of the cross-linking reactant sufficient to give the balloon a strength generally about equal to and in some cases perhaps greater than that of a balloon composed of the polyamide elastomer and comparably cross-linked by irradiation, but in the absence of any cross-linking reactant, agent or promoter.

In this third aspect, the balloon of the medical device preferably comprises a mixture of the polyamide elastomer and the cross-linking reactant which has been cross-linked by irradiation by an electron beam or by ultraviolet, or X- or gamma rays. Even more preferably, the balloon comprises a mixture of the polyamide elastomer and the cross-linking reactant which has been cross-linked by exposure to about 0.5 to about 20 megarads of radiation. The balloon is preferably formed by inflation of the mixture of the polyamide elastomer and the cross-linking reactant after the mixture has been cross-linked by irradiation.

As in the first aspect of the present invention, the balloon of the medical device of the second and third aspects of the present invention preferably comprises a polyester amide, a polyether ester amide or a polyether amide, and more preferably comprises a nylon block copolymer including polyether blocks separated by polyamide blocks, such as PEBAX® brand nylon block copolymer.

In a fourth aspect, the present invention is directed to a process for assembling a medical device, the medical device comprising an expandable balloon, and the process comprising: creating a mixture of a polyamide elastomer and at least one additional cross-linking reactant, the cross-linking reactant comprising: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether; (b) a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis,cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein; cross-linking the mixture of the polyamide elastomer and the at least one additional reactant by exposing the mixture to a suitable fluence of radiation; and forming the cross-linked mixture into the balloon. In a fifth aspect of the present invention, this process is instead carried out with at least one additional cross-linking reactant comprising diallyl phthalate or meta-phenylene dimaleimide.

The process of the present invention for assembling the medical device is preferably carried out with an amount of the cross-linking reactant sufficient to give the balloon a strength generally about equal to, and perhaps in some cases greater than, that of a balloon composed of the polyamide elastomer and comparably cross-linked by irradiation, but in the absence of any cross-linking reactant, agent or promoter. It is also preferred that the process is carried out with an amount of the cross-linking reactant which, when mixed with the polyamide elastomer and processed, causes the mixture from which the balloon is made to lack appreciable gelling during processing prior to irradiation and cross-linking. More preferably, the process is carried out with a mixture comprising about 1 to about 2 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material. Alternatively, the process can be carried out with about 1 to about 2 percent by weight diallyl phthalate or meta-phenylene dimaleimide.

Cross-linking of the mixture of the polyamide elastomer and the at least one additional reactant preferably comprises irradiating the mixture with an electron beam or with ultraviolet, X- or gamma rays. Irradiation is more preferably carried out at a total fluence of about 0.5 to about 20 megarads.

The process of the present invention is preferably carried out with the polyamide elastomers described above. More preferably, the process of the present invention is carried out with a nylon block copolymer which includes polyether blocks separated by polyamide blocks, such as PEBAXOR® brand nylon block copolymer. When the process is carried out with an aromatic molecule containing at least two ring substituents, each of the ring substituents having labile hydrogens at a benzylic site therein, it is preferred that the molecule is selected from the class consisting of 1,3,5 triethyl benzene; 1,2,4 triethyl benzene; and 1,3,5 triisopropyl benzene. Without regard to the specific polyamide elastomer and the at least one additional reactant employed in the present invention, however, it is preferred that the mixing of them is carried out by compounding (including such steps as melting, mixing and extruding, for example) or by blending.

The process of the present invention for making a medical device preferably further comprises forming the mixture of the polyamide elastomer and the at least one additional reactant into tubing, from which the balloon is formed. It is further preferred that the tubing is formed by extruding the mixture of the polyamide elastomer and the at least one additional reactant. Most preferably, the mixture of the polyamide elastomer and the at least one additional reactant is then formed into the balloon by inflation of the tubing. The process of the present invention can further comprise connecting the balloon so formed to a catheter shaft, for example, by adhesion or thermal bonding.

In a sixth aspect, the present invention is directed to a process for assembling a medical device, the medical device comprising an expandable balloon, and the process comprising: creating a mixture of a nylon block copolymer and no more than about 1.5 percent by weight of at least one additional cross-linking reactant, the cross-linking reactant comprising triallyl cyanurate or triallyl isocyanurate; cross-linking the mixture of the polyamide elastomer and the at least one additional reactant by exposing the mixture to a suitable fluence of radiation; and forming the cross-linked mixture into the balloon.

Other than the use of these two specific cross-linking reactants at the specified amounts, the preferred details of carrying out the process of this sixth aspect of the present invention are very comparable to the details of carrying out the process of the fourth aspect of the invention. Most notably, cross-linking of the mixture of the polyamide elastomer and the at least one additional reactant preferably comprises irradiating the mixture with an electron beam or with ultraviolet, X- or gamma rays. Irradiation is more preferably carried out at a total fluence of about 0.5 to about 20 megarads. The balloon is preferably formed by inflation of a tubing extruded from the mixture of the polyamide elastomer and the at least one cross-linking reactant, the tubing being irradiated before the balloon is formed from it. The process of the sixth aspect of the present invention is most preferably carried out with a nylon block copolymer including polyether blocks separated by polyamide blocks, such as PEBAX® brand nylon block copolymer.

In a seventh aspect, the present invention is directed to a medical device comprising: a catheter shaft; and an expandable balloon carried by the catheter shaft; wherein the balloon comprises an irradiation cross-linked mixture of a polyamide elastomer and at least one additional cross-linking reactant. This aspect of the invention may instead be considered as an improvement in a medical device comprising a catheter shaft and an expandable balloon carried by the catheter shaft, characterized in that the balloon comprises an irradiation cross-linked mixture of a polyamide elastomer and at least one additional cross-linking reactant.

As indicated above, the medical device of the present invention possesses significant advantages over prior devices for dilating a narrowing or obstruction in a vessel or lumen in a patient, and for deploying a stent across the site of such a narrowing or obstruction to prevent its restenosis. The balloon of the device of the present invention has a generally improved combination of strength (for example, greater tensile strength, burst pressure and/or puncture resistance) and compliance (the ratio of balloon diameter growth to balloon pressure). Gelling during its manufacture, if present, is limited to an acceptable level. The balloon of the device of the present invention is made from materials which meet a variety of desirable processing criteria, including thermal stability, non-toxicity, non-volatility, high boiling point (preferably, solid at room temperature), high flash point, insensitivity to moisture and commercial availability. A second polyamide elastomer or another polyamide (such as nylon) may be added in a minor amount (less than 50 percent by weight or mole fraction), but is not required.

The principle disclosed above, irradiation cross-linking a polymeric material (such as a polyamide elastomer) in the presence of at least one additional cross-linking reactant, has other practical uses and can meet the other problems mentioned above, problems not specifically addressed by the balloon catheter of the aspects disclosed above. More particularly, while a variety of medical devices are presently known in which two or more pieces having different chemical or mechanical properties are attached or affixed to one another, each piece having properties suited to the performance of a desired function, the principle of the present invention permits a single piece in a medical device to possess different functional properties at different locations on it. This result is achieved by altering the durometer of the single piece at one or more locations via selective cross-linking of the single piece at that location or those locations. "Durometer" is again broadly defined as above, and includes stiffness and resistance to lateral deformation, as well as related functional properties such as durometer hardness, modulus of elasticity and flexural modulus. The present invention thereby avoids the problems associated with medical devices having different pieces of different durometer, such as being susceptible to kinking where the different pieces join, and the difficulty of joining different pieces of small diameter (especially below about 1 mm outside diameter).

In a first additional aspect, the present invention is directed to a medical device comprising a unitarily and continuously formed portion having a varying durometer. "Unitarily and continuously" means more than merely securing pieces of different durometer to one another. Instead, the unitary, continuous material employed in the present invention is a single piece, even though the chemical composition or structure of the material may be somewhat modified along the length of the piece (due to selective cross-linking). This stands in direct contrast to prior devices in which discrete parts having different durometers are secured to one another. "Durometer" is used in the broad sense identified above. "Varying" means that the unitarily and continuously formed portion possesses different durometers at at least two different locations of the portion. Such different durometers can arise from the presence of cross-linking at one location and the absence of cross-linking at the other location, or from the presence of different degrees of cross-linking at the two different locations. The latter can be brought about by exposing the two different locations to different total fluences of cross-linking irradiation.

The unitarily and continuously formed portion of the medical device of the present invention can comprise a tubular portion and an inflatable balloon. The inflatable balloon is preferably a separate piece connected to the tubular portion, although the inflatable balloon can be unitarily and continuously formed with the tubular portion. In the former case, the tubular portion itself has a varying durometer, while in the latter case, the inflatable balloon and the tubular portion have different durometers. Instead of a balloon, the medical device can comprise an anchor structure unitarily and continuously formed with the tubular portion, the anchor structure and the tubular portion having different durometers. The anchor structure can comprise a malecot, a pigtail, a loop or a comparable structure for maintaining the position of the medical device in the patient.

The tubular portion can comprise a catheter shaft, for example, a catheter shaft having at least first and second catheter shaft segments of different durometer, the first and second catheter shaft segments being unitarily and continuously formed. Preferably, one of the at least first and second catheter shaft segments comprises a catheter tip while the other of the catheter shaft segments comprises a catheter body. In general, the catheter body preferably has a greater durometer than the catheter tip, although there may be alternative situations in which it is preferred that the catheter tip has a greater durometer than the catheter body.

The catheter tip can be the anchor structure mentioned above or can be an inflatable balloon. The medical device of the present invention is configured as a needle set, however, and in such a case the catheter tip preferably includes a distal end and a step or ledge formed in the catheter tip near the distal end. "Step" and "ledge" can be considered synonymous for the purposes of the present invention, as they each perform the same function in the present invention. The medical device of the present invention then further comprises a needle receivable in the catheter shaft, the needle bearing on it a ring, collar or enlargement engageable with or abuttable against the step or ledge in the catheter tip. "Ring," "collar" and "enlargement" can similarly be considered synonymous for the purposes of the present invention, since they each perform the same function in the present invention.

In yet a further alternative embodiment, the unitarily and continuously formed portion of the medical device of the present invention can comprise at least first and second unitarily and continuously formed parts having different durometers, and a transition zone of continuously varying durometer connecting the first and second parts, the transition zone being unitarily and continuously formed with the first and second parts. The first or second part of the unitarily and continuously formed portion can be the catheter tip or anchor structure disclosed above, a proximal or distal catheter segment or the inflatable balloon disclosed below. The transition zone can of course be absent, that is, it may extend only so far as may result from diffraction of the cross-linking irradiation at the edge of a shield which protects one of the first or second parts from irradiation. Alternatively, the unitarily and continuously formed portion can extend longitudinally, and the durometer of the portion can vary continuously along the entire length of the portion.

The medical device of the present invention is useful in forming infusion, drainage, diagnostic, therapeutic or balloon catheters, and more advantageously, in forming microcatheters having an outside diameter less than about 1 mm. Relating specifically to balloon catheters, for example, the medical device of the present invention can comprise a catheter shaft having an outer catheter shaft and an inner catheter shaft received in the outer catheter shaft, the outer catheter shaft comprising the unitarily and continuously formed portion disclosed above. Preferably, an inflatable balloon can be connected to the outer and inner catheter shafts. The outer catheter shaft can instead comprise an inflatable balloon unitarily and continuously formed with the unitarily and continuously formed portion, the inflatable balloon and the unitarily and continuously formed portion having different durometers. In either case, the inflatable balloon has a distal end sealed against the inner catheter shaft so that the space between the inner and outer catheter shafts serves as a lumen for the introduction and removal of pressurized fluid for inflation and deflation of the balloon.

The unitarily and continuously formed portion of the medical device of the present invention preferably generally comprises any of the balloon materials described herein. Thus, the unitarily and continuously formed portion preferably comprises an irradiation cross-linkable mixture of a polyamide elastomer and at least one additional cross-linking reactant. It should be noted that it is appropriate in these additional aspects of the invention to describe the material as "cross-linkable" rather than "cross-linked," because one part or another of the unitarily and continuously formed portion may not be cross-linked at all.

The at least one additional cross-linking reactant can comprise: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether; (b) a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis,cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein; the unitarily and continuously formed portion then comprising at least first and second parts unitarily and continuously formed with one another, at least one of the first and second parts being exposed to cross-linking irradiation. Preferably, the mixture comprises about 1 to about 3 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material.

Without regard to the specific polyamide elastomer or additional cross-linking reactant employed, the unitarily and continuously formed portion can comprise at least first and second parts unitarily and continuously formed with one another, at least one of the first and second parts being exposed to cross-linking irradiation, or the first and second parts being exposed to different amounts of cross-linking irradiation. Preferably, the unitarily and continuously formed portion comprises an amount of the at least one cross-linking reactant sufficient to give the unitarily and continuously formed portion a strength generally about equal to that of a unitarily and continuously formed portion composed of the polyamide elastomer and comparably cross-linked by irradiation, but in the absence of any cross-linking reactant, agent or promoter.

Cross-linking of the unitarily and continuously formed portion, in part or in whole, is brought about in any convenient or conventional manner, for example, by irradiation with an electron beam or with ultraviolet, X- or gamma rays. "In part" refers not to cross linking which is brought about at least in part by the indicated forms of irradiation, but rather means merely that at least part of the mixture making up the portion (even if not all of it) has been irradiation cross-linked. Preferably, the unitarily and continuously formed portion comprises a mixture of the polyamide elastomer and the at least one cross-linking reactant which has been cross-linked, at least in part, by exposure to about 0.5 to about 60 megarads of radiation, preferably about 30 megarads. It should be noted that degradation of some of the mixtures disclosed herein may begin to occur at the 55 to 60 megarad level.

As an aside, it should be noted that it is preferred that the amount of the at least one additional cross-linking reactant be uniform throughout the mixture making up the unitarily and continuously formed portion of the medical device. Varying the degree of cross-linking is then conveniently achieved by varying the fluence of irradiation to which the parts of the portion are exposed. It is certainly possible, however, that there might be circumstances under which it would be desirable to use a non-uniform mixture, and such use is contemplated as falling within the scope of the present invention.

The mixture from which the unitarily and continuously formed portion of the medical device of the present invention is fabricated can alternatively preferably comprise an irradiation cross-linkable mixture of a polyamide elastomer and an aromatic molecule containing at least two ring substituents, each of the ring substituents having labile hydrogens at a benzylic site therein, selected from the class consisting of 1,3,5 triethyl benzene; 1,2,4 triethyl benzene; and 1,3,5 triisopropyl benzene. The mixture preferably comprises at least one polyamide elastomer selected from the class consisting of polyester amides, polyether ester amides and polyether amides, and more preferably comprises a nylon block copolymer. Even more preferably, the mixture comprises a nylon block copolymer including polyether blocks separated by polyamide blocks.

As a further alternative, the unitarily and continuously formed portion of the medical device of the present invention preferably comprises an irradiation cross-linkable mixture of a polyamide elastomer and about 0.25 to about 5 percent by weight of triallyl cyanurate or triallyl isocyanurate as the at least one additional cross-linking reactant. Yet further, the at least one cross-linking reactant can instead preferably comprise diallyl phthalate or meta-phenylene dimaleimide, more preferably at about 1 to about 2 percent by weight in the mixture.

The most preferable mixture for use in the medical device of the present invention may be a mixture of a nylon block copolymer including polyether blocks separated by polyamide blocks, and about 3 percent by weight triallyl isocyanurate. Such a mixture preferably also includes up to about 25 percent by weight of a nylon, more preferably about 10 percent by weight nylon.

Without regard to its particular composition, however, the unitarily and continuously formed portion of the medical device of the present invention can comprise a tubular portion and an inflatable balloon unitarily and continuously formed with the tubular portion, the inflatable balloon being formed by inflation of the mixture of the polyamide elastomer and the at least one cross-linking reactant after at least part of the mixture has been cross-linked by irradiation.

In a second additional aspect, the present invention is directed to a medical device comprising a unitarily and continuously formed portion having a varying durometer, and a catheter shaft having an outer catheter shaft and an inner catheter shaft received in the outer catheter shaft, the outer catheter shaft comprising the unitarily and continuously formed portion; wherein the outer catheter shaft further comprises an inflatable balloon unitarily and continuously formed with the unitarily and continuously formed portion, the inflatable balloon and the unitarily and continuously formed portion having different durometers; and wherein the unitarily and continuously formed portion comprises an irradiation cross-linkable mixture of a nylon block copolymer including polyether blocks separated by polyamide blocks, and about 3 percent by weight triallyl isocyanurate. This aspect of the present invention is particularly useful in forming balloon microcatheters, having an outside diameter of less than about 1 mm. The inflatable balloon can alternatively be a distinct piece separate from the catheter shaft, connected to it but not unitarily and continuously formed with it.

In a third additional aspect, the present invention is directed to a medical device comprising a unitarily and continuously formed portion having a varying durometer, the unitarily and continuously formed portion comprising a catheter shaft having at least first and second catheter shaft segments of different durometer, the first and second catheter shaft segments being unitarily and continuously formed; wherein one of the at least first and second catheter shaft segments comprises a catheter tip and the other of the at least first and second catheter shaft segments comprises a catheter body, the catheter body having a greater durometer than the catheter tip; and wherein the unitarily and continuously formed portion comprises an irradiation cross-linkable mixture of a nylon block copolymer including polyether blocks separated by polyamide blocks, and about 3 percent by weight triallyl isocyanurate. The catheter tip may of course be the anchor structure or part of a needle set.

In a fourth additional aspect, the present invention is directed to a process for assembling a medical device, the medical device comprising a unitarily and continuously formed portion having a varying durometer, and the process comprising: creating an irradiation cross-linkable mixture of a polyamide elastomer and at least one additional cross-linking reactant; forming the mixture into a unitarily and continuously formed portion; and exposing the unitarily and continuously formed portion, at least in part, to cross-linking irradiation. The mixture is preferably formed into a tubular portion suited to any of a variety of purposes.

The step of forming the unitarily and continuously formed portion can, for example, comprise forming a portion intended for use as an inflatable balloon unitarily and continuously with the tubular portion, wherein the exposing step comprises exposing at least one of the tubular portion and the portion intended for use as an inflatable balloon, to cross-linking irradiation. The process of the present invention then preferably additionally comprises heating and applying pressure to the portion intended for use as an inflatable balloon so as to form a suitable inflatable balloon from that portion. The preferred processing conditions are the same as disclosed with respect to prior aspects of the invention, and as described in detail below. The resulting tubular portion and unitarily and continuously formed inflatable balloon have different durometers. The inflatable balloon can alternatively be a distinct piece separate from the catheter shaft, connected to it but not unitarily and continuously formed with it.

Alternatively, the step of forming the unitarily and continuously formed portion can instead preferably comprise forming an anchor structure unitarily and continuously with the tubular portion, wherein the exposing step comprises exposing at least one of the anchor structure and the tubular portion to cross-linking irradiation. The step of forming an anchor structure can comprise forming a malecot, a pigtail, a loop or the like. As above, the resulting tubular portion and unitarily and continuously formed anchor structure have different durometers, improving anchoring of the tubular portion in the patient.

As a further alternative, the step of forming the unitarily and continuously formed portion can comprise forming a catheter shaft from the mixture, the catheter shaft preferably having at least first and second unitarily and continuously formed catheter shaft segments. The exposing step then preferably comprises exposing at least one of the first and second catheter shaft segments to cross-linking irradiation, to give them different durometers. The exposing step can comprise exposing only one of the first and second catheter shaft segments to irradiation, or can comprise exposing the first and second catheter shaft segments to different amounts of cross-linking irradiation.

The step of forming a catheter shaft can preferably further comprise forming one of the first and second catheter shaft segments into a catheter tip and the other of the first and second catheter segments into a catheter body. Either or both of the catheter body and the catheter tip can then be exposed to cross-linking irradiation, giving them different durometers. Prior to such exposure, however, the catheter tip can be formed so as to give it desired characteristics. For example, the step of forming a catheter shaft can further comprise forming a step or ledge in the catheter tip near a distal end of the catheter tip, and the process further comprise introducing a needle into the catheter shaft, the needle bearing on it a ring, collar or enlargement engageable with or abuttable against the step or ledge in the catheter tip. As with needle sets having a discrete catheter tip of harder material, the needle set resulting from the process of the present invention is less subject to sliding of the catheter body with respect to the needle during introduction into a patient ("accordioning"), while avoiding the drawbacks associated with attempting to affix a discrete catheter tip to the catheter body.

The change of durometer between first and second unitarily and continuously formed parts of the unitarily and continuously formed portion can be sharp, achieved simply by placing a shield of uniform thickness between the unitary and continuously formed portion and a source of cross-linking irradiation, prior to the exposing step. It is preferred, however, that the exposing step instead comprises exposing a unitarily and continuously formed transition zone between the first and second parts to a continuously varying amount of cross-linking irradiation. This can be achieved, for example by placing a shield of varying density between the unitarily and continuously formed portion and a source of cross-linking irradiation, prior to the exposing step. The shield can have a taper which attenuates the exposure to irradiation (and thereby attenuates cross-linking) in the transition zone covered by the taper. A continuous change over part or all of the longitudinal extent of the unitarily and continuously formed portion can be achieved with a similar shield.

This aspect of the invention can also be employed to form a balloon catheter, and in particular, a balloon microcatheter having an outer diameter of about 1 mm or less. In such a process, the forming step comprises forming a catheter shaft comprising an outer catheter shaft and an inner catheter shaft received in the outer catheter shaft, the outer catheter shaft comprising the irradiation cross-linkable mixture. The forming step further preferably comprises unitarily and continuously forming with the outer catheter shaft a portion intended for use as an inflatable balloon, wherein the exposing step is carried out so as to provide different durometers to the outer catheter shaft and the portion intended for use as an inflatable balloon by exposing at least one of the outer catheter shaft and the portion intended for use as an inflatable balloon to cross-linking irradiation. The process further preferably comprises heating and applying pressure to the portion intended for use as an inflatable balloon so as to form an inflatable balloon from that portion. The inner catheter shaft is then inserted into the outer catheter shaft and through the balloon portion, and the distal end of the balloon secured to and fluidly sealed in a conventional fashion to the inner catheter shaft. A space between the outer and inner catheter shafts defines the lumen for the introduction and removal of pressurized inflation fluid to the inflatable balloon. Alternatively, however, the inflatable balloon can be a separate piece connected to the outer and inner catheter shafts, unitarily and continuously formed with neither of them.

Expressed in its most general terms, in the process of the present invention, the forming step is preferably carried out so as to yield a unitarily and continuously formed portion comprising at least first and second parts unitarily and continuously formed with one another, wherein the exposing step comprises exposing at least one of the first and second parts to cross-linking irradiation. The different parts of the unitarily and continuously formed portion are thereby given different durometers. This is most easily achieved by exposing only one of the first and second parts of the unitarily and continuously formed portion to cross-linking irradiation. It may be desirable, however, that the exposing step comprise exposing the first and second unitarily and continuously formed parts to different amounts of cross-linking irradiation.

The process of the present invention is preferably carried out employing any of the cross-linkable mixtures disclosed herein. Accordingly, the process of the present invention can be carried out with a cross-linking reactant comprising: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether; (b) a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis,cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein. In such a case, the process is preferably carried out with a mixture comprising about 1 to about 2 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material.

The process of the present invention is preferably carried out with an amount of the at least one cross-linking reactant sufficient to give the unitarily and continuously formed portion a strength generally about equal to that of a unitarily and continuously formed portion composed of the nylon block copolymer and comparably cross-linked by irradiation, but in the absence of any cross-linking reactant, agent or promoter. The exposing step of the present invention preferably comprises irradiating the mixture with an electron beam or with ultraviolet, X- or gamma rays, at a total fluence of about 0.5 to about 60 megarads, preferably about 30 megarads.

The mixing of the polyamide elastomer and the at least one additional reactant can be conveniently carried out by compounding, while the tubular portion can be formed by extruding the mixture of the polyamide elastomer and the at least one additional reactant.

The process of the present invention is preferably carried out with at least one polyamide elastomer selected from the class consisting of polyester amides, polyether ester amides and polyether amides. The process is more preferably carried out with a polyamide elastomer comprising a nylon block copolymer, most preferably with a nylon block copolymer including polyether blocks separated by polyamide blocks. It is probably most preferable that the process be carried out with about 3 percent by weight triallyl isocyanurate as the additional cross-linking reactant in a mixture which also includes about 10 percent by weight nylon.

The process of the present invention can instead be carried out with an irradiation cross-linkable mixture of a polyamide elastomer and an aromatic molecule containing at least two ring substituents, each of the ring substituents having labile hydrogens at a benzylic site therein, selected from the class consisting of 1,3,5 triethyl benzene; 1,2,4 triethyl benzene; and 1,3,5 triisopropyl benzene.

It is alternatively preferred that the process of the present invention be carried out with a mixture of a polyamide elastomer and no more than about 5 percent by weight of at least one additional cross-linking reactant, the cross-linking reactant comprising triallyl cyanurate or triallyl isocyanurate. The process can also be carried out with a mixture comprising about 1 to about 2 percent by weight of a cross-linking reactant comprising diallyl phthalate or meta-phenylene dimaleimide.

In a fifth and final additional aspect, the present invention is directed to a process for assembling a medical device, the medical device comprising a unitarily and continuously formed portion having a varying durometer, and the process comprising: creating an irradiation cross-linkable mixture of a polyamide elastomer and at least one additional cross-linking reactant; forming the mixture into a unitarily and continuously formed portion; and exposing the unitarily and continuously formed portion, at least in part, to cross-linking irradiation; wherein the step of forming the portion comprises forming the mixture into a tubular portion; wherein the forming step is carried out so as to yield a unitarily and continuously formed portion comprising at least first and second parts unitarily and continuously formed with one another, and the exposing step comprises exposing at least one of the first and second parts to cross-linking irradiation; wherein the exposing step comprises irradiating the mixture with an electron beam at a total fluence of about 0.5 to about 60 megarads; wherein the mixing of the polyamide elastomer and the at least one additional reactant is carried out by compounding, and wherein the tubular portion is formed by extruding the mixture of the polyamide elastomer and the at least one additional reactant; and wherein the process is carried out with a mixture comprising: a nylon block copolymer including polyether blocks separated by polyamide blocks, about 3 percent by weight triallyl isocyanurate and about 10 percent by weight nylon.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 4 is a side view of the medical device of another preferred embodiment of the present invention, and of apparatus for its manufacture;

FIG. 5 is a partial cross-sectional view of a portion of another preferred embodiment of the present invention;

DETAILED DESCRIPTION OF THE INVENTION

Figure 1:
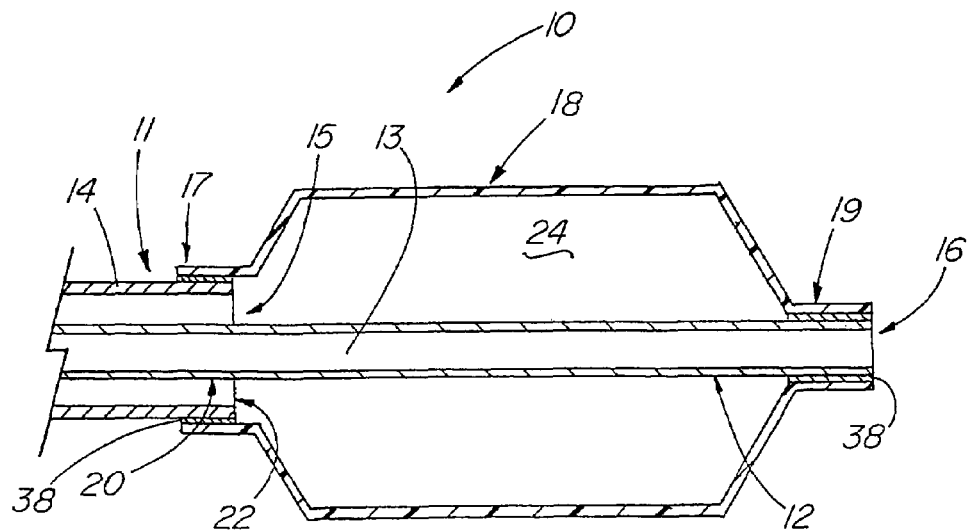
FIG. 1 is a partial cross-sectional view of the medical device of the preferred embodiment of the present invention.

With reference first to FIG. 1, an embodiment of a medical device 10 according to the present invention is thereshown, useful for dilating a narrowing or obstruction in a vessel or lumen in a patient, and/or for deploying a stent (not shown in the Figures) across the site of such a narrowing or obstruction to prevent its restenosis. The medical device 10 of the present invention first comprises a catheter shaft 11. The catheter shaft 11 is preferably a multi-element shaft, and preferably comprises an inner catheter shaft 12 received in and extending longitudinally through a lumen 20 in an outer catheter shaft 14. The catheter shaft 11 could alternatively comprise a single catheter shaft (not shown) having at least one lumen formed longitudinally therein. The inner and outer catheter shafts 12 and 14 preferably comprise medical grade polyethylene, polyamide or other suitable medical grade materials, and are of a diameter or French size suited to the particular procedure in which it is intended to use the device 10. The inner and outer catheter shafts 12 and 14 can comprise the same or different such materials.

The device 10 of the present invention also comprises an inflatable balloon 18 carried on the catheter shaft 11. The balloon 18 comprises an irradiation cross-linked mixture of a polyamide elastomer and at least one additional cross-linking reactant, the nature of the mixture and its cross-linking being described in more detail below. The balloon 18 is dimensioned and adapted for the particular procedure in which it is to be employed. Balloon length and inflation diameters suited to various procedures are well known, and for brevity need not be recited here.

The balloon 18 is preferably formed separately from the catheter shaft 11, and separately from the inner and outer catheter shafts 12 and 14. The balloon 18 is more preferably affixed at its proximal end 17 to the distal end 15 of the outer catheter shaft 14, and at its distal end 19 to the distal end 16 of the inner catheter shaft 12. Affixing can occur by use of a suitable medical grade adhesive 38, or by thermal bonding.

The lumen 20 defined in the outer shaft 14 permits the supply of an inflation fluid from a supply (not shown) and to the interior 24 of the balloon 18. More particularly, the catheter shaft 14 has a lumen end port 22 defined at its distal end 15, placing the balloon interior 24, the catheter shaft lumen 20 and the inflation fluid supply in fluid communication with one another. The balloon 18 may carry on it a stent of conventional design (not shown), expanded or permitted to expand upon inflation of the balloon 18.

Either or both of the inner and outer catheter shafts 12 and 14 can include one or more other lumens for any of a variety of conventional purposes. For example, the inner catheter shaft 12 can include a lumen 13 defined longitudinally therein for the introduction or passage of a conventional wire guide therethrough. In use of the medical device 10 of the present invention, this wire guide would first be advanced across the narrowing or obstruction to be treated, and the balloon 18 of the medical device 10 then advanced along this wire guide until the balloon 18 was positioned across the narrowing or obstruction. Inflation of the balloon 18 then widens the narrowing or obstruction. If the medical device 10 has been supplied with a stent, such inflation deploys the stent at the site of the narrowing or obstruction, preventing restenosis of the site. Of course, any additional lumens in the inner and outer catheter shafts 12 and 14 can be employed for other conventional purposes, such as fluid drainage or injection, or the passage of another catheter or other medical device or instrument.

As indicated above, the balloon 18 comprises an irradiation cross-linked mixture of a polyamide elastomer and at least one additional cross-linking reactant which acts to covalently link the chains of the polyamide elastomer. The polyamide elastomer can be a polyester amide, a polyether ester amide or a polyether amide. Specific commercial examples of such materials include ESTAMID®, PEBAX®, VESTAMID®, GRILAMID® and GRILON® brand polymers. The polyamide elastomer used to make the balloon 18 is preferably a nylon block copolymer. Nylon block copolymers expected to be useful in making the balloon 18 of the medical device 10 of the present invention include polyamide blocks separated by polyether blocks or other elastomeric blocks or segments, such as polyesters, hydrocarbons or polysiloxanes. Preferably, the polyamide elastomer is an polyester amide, a polyether ester amide or a polyether amide as described above. More preferably, the nylon block copolymer employed in the mixture from which the balloon 18 is formed comprises a nylon block copolymer including polyamide blocks separated by polyether blocks. Most preferably, the nylon block copolymer is PEBAX® brand nylon block copolymer. Although probably not preferred, the mixture from which the balloon 18 of the medical device 10 of the present invention can also comprise a minor proportion (less than 50 percent by weight or mole fraction) of a second polyamide elastomer or another polyamide (such as nylon) similarly capable of being cross-linked by the at least one additional cross-linking reactant.

The at least one additional cross-linking reactant can comprise any of a variety of materials. For example, the at least one additional cross-linking reactant can comprise a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether. The mixture from which the balloon 18 is formed preferably comprises about 1 to about 2 percent by weight of such a difunctional material. Alternatively, the at least one additional cross-linking material can comprise a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether. The mixture from which the balloon 18 is formed then preferably comprises about 0.5 to about 1.5 percent by weight of such a trifunctional material. The amount of tri-functional material required for the balloon 18 will likely be somewhat less than the amount of difunctional material required, because the additional functional group of the trifunctional material provides an additional site for the material to bond to the chains of the polyamide elastomer.

The at least one additional cross-linking reactant can alternatively comprise a tetrafunctional material selected from the class consisting of tetraallyl cis,cis,cis,cis-cyclopentane-1,2,3,4-tetracarboxylate; and N,N,N',N'-tetraallylethylenediamine. The mixture from which the balloon 18 is formed then preferably comprises about 0.01 to about 1 percent by weight of the tetrafunctional material. The dramatically lower value is possible because the fourth functional group may permit cross-linking to be achieved even more readily than with trifunctional materials; however, depending upon the sterics of the particular polyamide elastomer and the particular tetrafunctional material selected, such low values may not actually be enjoyed. The at least one additional cross-linking reactant can instead comprise an aromatic molecule containing at least two ring substituents, each of the ring substituents having labile hydrogens at a benzylic site therein.

The mixture from which the balloon 18 is formed then preferably comprises about 0.5 to about 1.5 percent by weight of the aromatic molecule containing at least two ring substituents, each of the ring substituents having labile hydrogens at a benzylic site therein. The aromatic molecule containing at least two ring substituents, each of the ring substituents having labile hydrogens at a benzylic site therein, is preferably selected from the class consisting of 1,3,5 triethyl benzene; 1,2,4 triethyl benzene; and 1,3,5 triisopropyl benzene. As indicated above, the aromatic molecule containing at least two ring substituents, each of the ring substituents having labile hydrogens at a benzylic site therein, may instead be any of a wide variety of suitably-substituted aromatic molecules; these three are preferred because they are commercially available at the present time. Finally, the at least one additional cross-linking reactant can comprise no more than about 1.5 percent by weight of triallyl cyanurate or triallyl isocyanurate, or about 1 to about 2 percent by weight of diallyl phthalate or meta-phenylene dimaleimide.

Without regard to the particular at least one additional cross-linking reactant employed, the mixture from which the balloon 18 is formed comprises an amount of the at least one additional cross-linking reactant sufficient to give the balloon 18 a strength generally about equal to, and in some cases perhaps greater than, that of a balloon composed of the polyamide elastomer and comparably cross-linked by irradiation, but in the absence of any cross-linking reactant, agent or promoter.

The mixture is preferably irradiated before the balloon 18 is formed by inflation as described below, or otherwise formed. The mixture of the polyamide elastomer and the at least one additional cross-linking reactant can be cross-linked by irradiation with an electron beam or with ultraviolet, X- or gamma rays, preferably with an electron beam since it may be more efficient and may achieve satisfactory cross-linking at lower fluences than the others. Preferably, the mixture is cross-linked by exposure to a total fluence of about 0.5 to about 20 megarads.

The general process for forming a balloon 18 from the mixture of the polyamide elastomer and the at least one additional cross-linking reactant, and incorporating such a balloon into a medical device 10, can now be readily understood. A familiarity with the principles of manufacturing balloons for medical devices and the associated regulatory requirements is presumed. Those skilled in the art of manufacturing balloons for medical devices should readily be able to adapt the general process described herein to the particular materials being employed.

In its simplest form, the process for assembling a medical device 10 comprising an expandable balloon 18 comprises the steps of creating a mixture of a polyamide elastomer and at least one additional cross-linking reactant as described above; cross-linking the mixture of the polyamide elastomer and the at least one additional cross-linking reactant by exposing the mixture to a suitable fluence of radiation; and forming the resulting cross-linked mixture into the balloon 18. The details of the preferred composition of the nylon block copolymer and the at least one additional cross-linking reactant, as well as the preferred types and fluences of irradiation, are recited above; for brevity, these will not be repeated.

Figure 3:
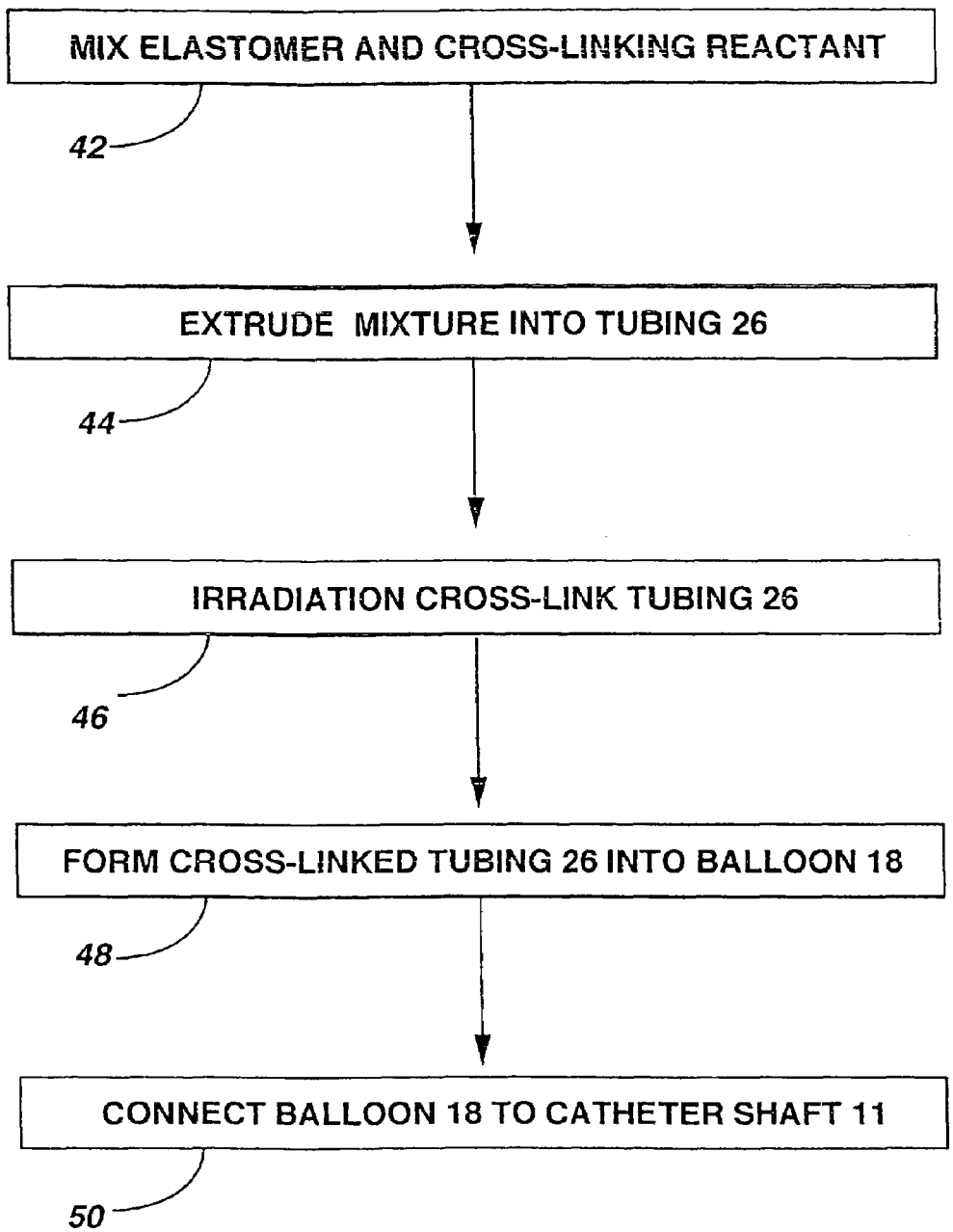
FIG. 3 is a flow chart of the process of assembling the medical device of the preferred embodiment of the present invention.

The process of the present invention can be carried out with any of a variety of specific process steps known to be useful for assembling balloon-type medical devices from materials other than the specific mixtures of polyamide elastomers and cross-linking reactants disclosed herein. Accordingly, the description of any particular steps or any specific apparatus for performing any particular steps should not be taken as limiting the scope of the broad process disclosed herein. For purposes of illustration, however, a preferred process according to the present invention for assembling the medical device 10 is shown in the flow chart of FIG. 3. First, the polyamide elastomer and the at least one additional cross-linking reactant are intimately mixed together (box 42). Such mixing is most conveniently carried out by compounding and/or blending the elastomer and the cross-linking reactant together. Next, the mixture of the polyamide elastomer and the at least one additional cross-linking reactant are formed into a shape suitable for irradiation and further processing. Conveniently, the mixture of the elastomer and the cross-linking reactant are extruded into the shape of a tubing 26 (box 44). Other extrusion shapes can be employed as needed or desired. The tubing 26 (or other form of the mixture) is then irradiated to cross-link the material (block 46). Irradiation is most conveniently carried out by exposing the tubing 26 to an electron beam or to a source of ultraviolet, X- or gamma rays, the electron beam probably being preferred.

Figure 2:
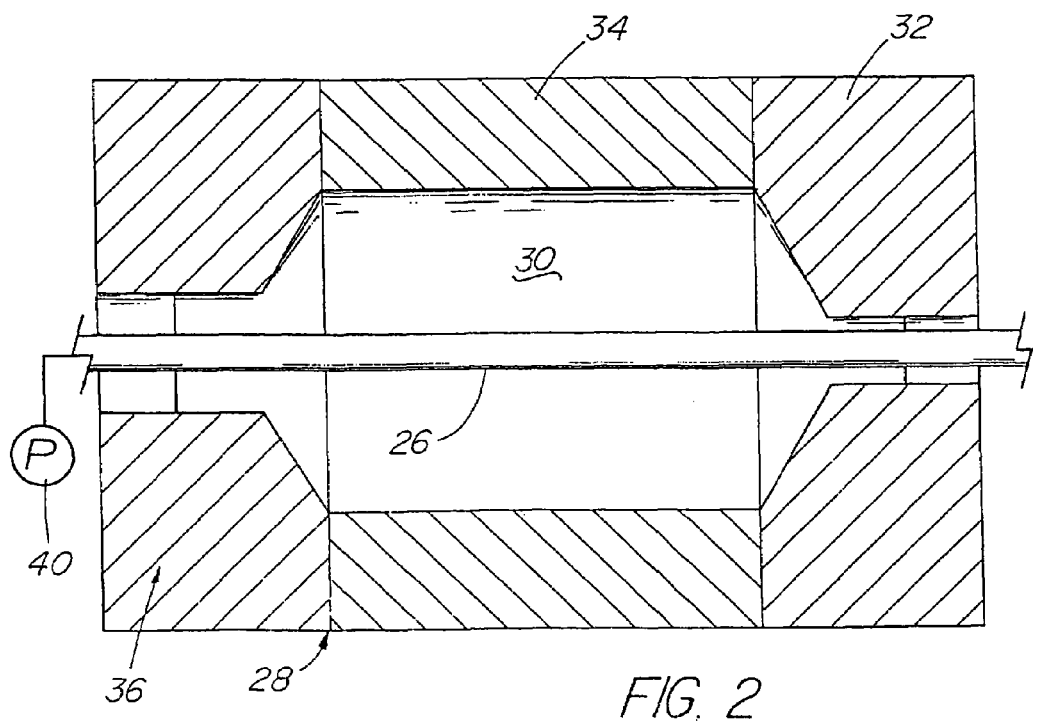
FIG. 2 is a partial cross-sectional view of a step in the process for assembling the medical device of the preferred embodiment of the present invention.

The cross-linked material, in the physical form of the tubing 26, is then formed into the balloon 18 (box 48). The tubing 26 is most conveniently formed into the balloon 18 by applying heat and an inflation medium or fluid to the tubing 26. A simplified view of an apparatus for performing this balloon-forming step is shown in FIG. 2. The tubing 26 is introduced into a heatable mold 28 having first, second and third mold parts 32, 34 and 36, whose facing surfaces define between them a mold cavity 30. The mold cavity is shaped and sized substantially the same as the ultimately desired shape and size of the balloon 18, shrinkage and other conventional molding concerns having been taken into account. The mold 28 is heated, thereby warming the tubing 26, and a source 40 of pressurized inflation medium is applied to an open end of the tubing 26 outside the mold 28. Sufficient inflation pressure is supplied from the source 40 to cause the tubing 26 to expand within the mold 28 until the tubing 26 contacts the facing surfaces of the mold parts 32, 34 and 36, and takes on the shape of the mold cavity 30. Pressure in the tubing 26 is then relieved, the tubing 26 deflated and removed from or allowed to exit the mold 28 for further processing as needed. Stretching of the tubing 26 and/or repeated heating or inflation of the tubing 26 can be performed in the conventional manner, as needed or as desired to achieve the balloon 18 (as a portion of the tubing 26).

Once the balloon 18 is formed as a part of the tubing 26, the balloon 18 is cut from the tubing 26 and connected to the catheter shaft 11 (box 50), for example, by affixing the proximal and distal ends 17 and 19 of the balloon 18 to the distal ends 16 and 15 of the inner and outer catheter shafts 12 and 14. Affixing can be carried out by use of the medical grade adhesive 38 described above, or by heat bonding.

The process of the present invention forming the medical device 10 is of course not limited to the particular steps described above. A wide variety of steps and methods for forming medical device balloons from other materials are well-known, and are expected to be useful in the assembly of the medical device 10. For example, molds having other than three pieces can be used; indeed, a single balloon for a medical device can be formed with no mold at all, just inflation of a parison having only an inlet for an inflation fluid, and no outlet.

EXAMPLES

A variety of examples of irradiation cross-linked mixtures of PEBAX® brand nylon block copolymer with differing amounts of triallyl cyanurate or triallyl isocyanurate ("% XL") as the at least one cross-linking reactant are disclosed in Tables 1 through 4 annexed hereto. The French size indicates the size of the tubing 26 from which the balloon 18 is made, while the Double Wall (in inches) indicates twice the wall thickness of the balloon 18 ultimately formed (the thickness of the opposing balloon walls when pressed together). In the Material Formulations column in the Tables, 7233SAO1 and 6333SNO1 refer to two different grades of PEBAX® brand copolymers. Formulations containing both grades thus constitute mixtures of two different copolymers. The particular nylon block copolymer mixtures used in the examples were specially ordered mixtures, mixtures which it is believed are not otherwise commercially distributed at this time. More specifically, it is believed that Foster Corporation, Dayville, Conn., commercially distributes (under the trade name FOSTALINK™) mixtures containing PEBAX® brand copolymer and 2 percent or more by weight of either triallyl cyanurate or triallyl isocyanurate. Mixtures containing 0.125 to 1.00 percent weight of either triallyl isocyanurate or triallyl isocyanurate were requested from Foster Corporation, and were used in the examples in the Tables. As an aside, it should be noted that it is not presently known which of the two materials, the triallyl cyanurate or the triallyl isocyanurate, was included in the FOSTALINK™ materials used in the examples.

A number of comparative examples are shown in the Tables, in which the triallyl cyanurate or triallyl isocyanurate is not present; in which the mixture of the nylon block copolymer and the at least one additional cross-linking reactant is not irradiated; in which the at least one additional cross-linking reactant is omitted; and in which nylon 12 is added to the nylon block copolymer at an indicated percentage by weight. Irradiation at the indicated fluence occurred by exposure to an electron beam; as indicated above, other forms of irradiation are expected to be less efficient than electron beam at performing the cross-linking desired in the present invention, and higher fluences of ultraviolet, X- or gamma rays may be required to achieve the same results.

Table 1 contains comparative examples of mixtures (Material Formulations) employed to form tubing of the indicated French size and diameters into balloons. Except for the last entry (which comprised solely nylon 6/6), the comparative examples of Table 1 were carried out with mixtures comprising a PEBAX® brand nylon block copolymer and 2 or 3 percent by weight of a triallyl cyanurate or triallyl isocyanurate; mixtures comprising a PEBAX® brand nylon block copolymer, 3 percent by weight of a triallyl cyanurate or triallyl isocyanurate and 10 percent by weight of a nylon 12; or mixtures comprising a PEBAX® brand nylon block copolymer and 10 percent by weight of a nylon 12, without any triallyl cyanurate or triallyl isocyanurate.

Table 2 contains comparative examples of mixtures comprising a nylon 12 with no cross-linking reagent; a PEBAX®) brand nylon block copolymer with no cross-linking reagent; and a PEBAX® brand nylon block copolymer with 2 percent by weight of a triallyl cyanurate or triallyl isocyanurate, as well as mixtures containing 3 percent by weight of a triallyl cyanurate or triallyl isocyanurate and further including a second PEBAX® brand nylon block copolymer or a nylon 12.

Table 3 contains further comparative examples of such mixtures.

Finally, Table 4 contains examples of mixtures useful for forming the balloon 18 of the medical device 10 of the present invention. More particularly, the mixtures of the examples shown in Table 4 comprise a PEBAX® brand nylon block copolymer and 0.125 to 1.00 percent by weight of a triallyl cyanurate or triallyl isocyanurate, irradiated by electron beam at total fluences of 0.5 to 7 megarads (comparative examples at 0.0 megarads also being included in Table 4).

It is believed that the data in Tables 1 through 4 demonstrate that a medical device 10 of the present invention, incorporating a balloon 18 comprising an irradiated mixture of a polyamide elastomer and at least one additional cross-linking reactant as defined herein, possesses significant advantages over prior medical devices incorporating balloons made of other materials. The present invention thus provides a medical device 10 which is particularly useful for dilating a narrowing or obstruction in a vessel or lumen in a patient, and for deploying a stent across the site of such a narrowing or obstruction to prevent its restenosis. The balloon 18 of the device 10 of the present invention has a generally improved combination of strength (for example, greater tensile strength, burst pressure and/or puncture resistance) and compliance in comparison to balloons in prior devices for these purposes. Gelling during the steps leading to manufacture of the balloon 18, if present, is limited to an acceptable level. The balloon 18 of the medical device 10 of the present invention is made from materials which meet a variety of desirable processing criteria, including thermal stability, non-toxicity, non-volatility, high boiling point (preferably, solid at room temperature), high flash point, insensitivity to moisture and commercial availability.

TABLE 1

| Parison French size (O.D.) | Material Desc. | Vendor Mat'l. Lot # | Lot # | Mat'l. Formulation | Avg. Tensile (lb.) | Std. Dev | Elongation | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|---|---|---|---|---|---|---|
| 4.7 | R & D 1102 | S66246 | P136575 | 7233SAO1 w/2% XL | 10.515 | 1.20 | 7.69 | 1.095 | 3 | 5 | 6.00 | 0.14 | 10.1 | 0.78 | 0.00125 | 6.75 |
| 4.7 | R & D 1102 | S66246 | P136575 | 7233SAO1 w/2% XL | 9.706 | 1.11 | 7.241 | 0.916 | 3 | 7 | 6.00 | 0.12 | 9.97 | 0.78 | 0.00125 | 6.8 |
| 6.1 | R & D 1102 | S66246 | P136573 | 7233SAO1 w/2% XL | 17.575 | 1.218 | 7.765 | 0.594 | | 5 | 5.00 | | | | | |

TABLE 1-continued

| Parison French size (O.D.) | Material Desc. | Vendor Mat'l. Lot # | Lot # | Mat'l. Formulation | Avg. Tensile (lb.) | Std. Dev | Elongation | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|---|---|---|---|---|---|---|
| 6.1 | R & D 1102 | S66246 | P136573 | 7233SAO1 w/2% XL | 18.725 | 1.48 | 8.943 | 0.672 | | 7 | 5.00 | | | | | |
| 3.4 | R & D 1137 | S68043 | P137420 | 7233SAO1 w/3% XL | 12.054 | 0.537 | 12.561 | 0.697 | | 0 | 4.00 | | | | | |
| 3.4 | R & D 1137 | S68043 | P137420 | 7233SAO1 w/3% XL | 10.5 | 0.786 | 7.84 | 0.829 | | 2.5 | 4.00 | | | | | |
| 3.4 | R & D 1137 | S68043 | P137420 | 7233SAO1 w/3% XL | 10.6 | 0.757 | 7.60 | 0.609 | 11.5 | 4 | 4.00 | 0.04 | 25 | 1.63 | 0.002 | 3.36 |
| 3.4 | R & D 1137 | S68043 | P137420 | 7233SAO1 w/3% XL | 10.6 | 0.757 | 7.60 | 0.509 | 11 | 4 | 4.00 | 0.036 | 26.2 | 1.58 | 0.002 | 3.38 |
| 5.5 | R & D 1137 | S68043 | P137423 | 7233SAO1 w/3% XL | 21.508 | 1.748 | 11.841 | 0.721 | | 0 | 6.00 | 0.21 | 13.2 | 0.4 | 0.00175 | 7.94 |
| 5.5 | R & D 1137 | S68043 | P137423 | 7233SAO1 w/3% XL | 20.549 | 1.648 | 7.65 | 0.831 | | 3 | 6.00 | 0.09 | 14.8 | 1 | 0.00225 | 6.54 |
| 5.5 | R & D 1137 | S68043 | P137423 | 7233SAO1 w/3% XL | 18.948 | 1.055 | 7.89 | 0.733 | | 5 | 6.00 | 0.083 | 15.4 | 0.9 | 0.00225 | 6.5 |
| 5.5 | R & D 1137 | S68043 | P137423 | 7233SAO1 w/3% XL | 20.072 | 1.185 | 7.50 | 0.658 | | 8 | 6.00 | 0.088 | 15.39 | 1.18 | 0.00225 | 8.51 |
| 5.5 | R & D 1137 | S68043 | P138587 | 7233SAO1 w/3% XL | 28.39 | 2.143 | 13.938 | 1.113 | 3 | 0 | 6.00 | 0.215 | 15.6 | 0.5 | 0.002 | 9.07 |
| 5.5 | R & D 1137 | S68043 | P138587 | 7233SAO1 w/3% XL | 27.893 | 2.179 | 10.392 | 0.952 | 7 | 3 | 6.00 | 0.085 | 18.2 | 2.8 | 0.0025 | 7.08 |
| 5.5 | R & D 1137 | S88043 | P138587 | 7233SAO1 w/3% XL | 25.765 | 1.73 | 9.237 | 0.727 | 8 | 5 | 6.00 | 0.075 | 18.5 | 1.95 | 0.0025 | 6.58 |
| 5.5 | R & D 1137 | S88043 | P138587 | 7233SAO1 w/3% XL | 25.766 | 1.73 | 9.237 | 0.727 | 8 | 5 | 6.00 | 0.069 | 19.05 | 1.17 | 0.0025 | 6.83 |
| 5.5 | R & D 1137 | S88043 | P138587 | 7233SAO1 w/3% XL | 25.766 | 1.73 | 9.237 | 0.727 | 7 | 5 | 6.00 | 0.052 | 20.29 | 1.3 | 0.0025 | 8.81 |
| 5.5 | R & D 1137 | S88043 | P138587 | 7233SAO1 w/3% XL | 26.842 | 2.385 | 9.319 | 0.947 | 9 | 7 | 6.00 | 0.079 | 19.8 | 0.96 | 0.0025 | 6.95 |
| 5.5 | R & D 1137 | S68043 | P138587 | 7233SAO1 w/3% XL | 22.977 | 2.01 | 7.533 | 0.753 | | 15 | 5.00 | | | | | |
| 5.5 | R & D 1137 | S68043 | P138587 | 7233SAO1 w/3% XL | 22.311 | 1.69 | 6.751 | 0.564 | | 25 | 6.00 | | | | | |
| 5.5 | R & D 1137 | S68043 | P138587 | 7233SAO1 w/3% XL | 19.907 | 0.976 | 5.213 | 0.284 | | 50 | 6.00 | | | | | |
| 5.5 | R & D 1137 | S68043 | P138587 | 7233SAO1 w/3% XL | 19.08 | 1.392 | 4.669 | 0.425 | | 75 | 6.00 | | | | | |
| 5.5 | R & D 1137 | S68043 | P138587 | 7233SAO1 w/3% XL | 17.714 | 0.817 | 3.468 | 0.228 | | 100 | 6.00 | | | | | |
| 5.5 | R & D 1138 | S88541 | P138614 | 10% PA12/86.5% 7233SAO1/ 3% XL | 26.639 | 1.379 | 12.414 | 0.735 | | 0 | 6.00 | | | | | |
| 5.5 | R & D 1138 | S68541 | P138614 | 10% PA12/86.5% 7233SAO1/ 3% XL | 22.232 | 0.477 | 7.97 | 0.497 | | 3 | 6.00 | | | | | |
| 5.5 | R & D 1138 | S68541 | P138614 | 10% PA12/86.5% 7233SAO1/ 3% XL | 22.612 | 1.001 | 8.273 | 0.552 | 10 | 5 | 6.00 | 0.065 | 17.6 | 2.5 | 0.003 | 6.31 |
| 5.5 | R & D 1138 | S68541 | P138614 | 10% PA12/86.5% 7233SAO1/ 3% XL | 20.807 | 1.229 | 7.08 | 0.691 | | 7 | 6.00 | | | | | |
| 5.5 | R & D 1138 | S68541 | P138614 | 10% PA12/86.5% 7233SAO1/ 3% XL | 18.537 | 1.109 | 5.882 | 0.432 | | 15 | 6.00 | | | | | |
| 5.5 | R & D 1138 | S68541 | P138614 | 10% PA12/86.5% 7233SAO1/ 3% XL | 18.44 | 1.286 | 4.872 | 0.544 | | 25 | 6.00 | | | | | |
| 5.5 | R & D 1138 | S68541 | P138614 | 10% PA12/86.5% 7233SAO1/ 3% XL | 13.388 | 0.804 | 1.585 | 1.332 | | 100 | 6.00 | | | | | |
| 5.5 | R & D 1157 | S69481 | P138591 | 7233SAO1 w/10% PA12 | 19.372 | 0.29 | 8.635 | 0.191 | 3 | 3 | 6.00 | 0.19 | 15.73 | 0.451 | 0.002 | 8.74 |
| 5.5 | R & D 1157 | S69481 | P138591 | 7233SAO1 w/10% PA12 | 18.732 | 0.348 | 8.082 | 0.326 | 3 | 5 | 6.00 | 0.253 | 15.7 | 0.48 | 0.00225 | 9.01 |

TABLE 1-continued

| Parison French size (O.D.) | Material Desc. | Vendor Mat'l. Lot # | Lot # | Mat'l. Formulation | Avg. Tensile (lb.) | Std. Dev | Elongation | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|---|---|---|---|---|---|---|
| 5.5 | R & D 1157 | S69481 | P138591 | 7223SAO1 w/10% PA12 | 18.831 | 1.203 | 8.358 | 0.657 | 3 | 7 | 6.00 | 0.173 | 14.81 | 0.528 | 0.0015 | 8.43 |
| 5.5 | R & D 1157 | S69481 | P138591 | 7233SAO1 w/10% PA12 | 19.939 | 0.779 | 8.294 | 0.459 | 3 | 15 | 6.00 | 0.189 | 13.23 | 0.483 | 0.0015 | 8.35 |
| 5.5 | R & D 1157 | S69481 | P138591 | 7233SAO1 w/10% PA12 | 17.404 | 0.71 | 7.569 | 0.491 | | 25 | 6.00 | | | | | |
| 5.5 | R & D 1157 | S69481 | P138591 | 7233SAO1 w/10% PA12 | 15.892 | 0.868 | 5.476 | 0.395 | | 50 | 6.00 | | | | | |
| 5.5 | R & D 1157 | S69481 | P138591 | 7233SAO1 w/10% PA12 | 12.152 | 0.641 | 1.447 | 2.057 | | 100 | 6.00 | | | | | |
| 5.5 | 40080 | S64330 | P138669 | Nylon 6/8 0% XL | 38.336 | 2.184 | 11.577 | 0.773 | | 0 | 6.00 | | | | | |

TABLE 2

| Parison French size (O.D.) | Material Desc. | Vendor Mat'l. Lot # | Lot # | Mat'l. Formulation | Avg. Tensile (lb.) | Std. Dev | Elongation |
|---|---|---|---|---|---|---|---|
| 5.5 | 40140 | S68802 | P138661 | Nylon 12 0% XL | 22.116 | 0.84 | 7.841 |
| 5.8 | R & D 1102 | S66246 | P139014 | 7233SAO1 w/2% XL | 27.313 | 0.701 | 13.113 |
| 5.8 | R & D 1102 | S66246 | P139014 | 7233SAO1 w/2% XL | 25.482 | 1.427 | 9.972 |
| 5.8 | R & D 1102 | S66246 | P139014 | 7233SAO1 w/2% XL | 24.93 | 1.547 | 9.32 |
| 5.8 | R & D 1102 | S66246 | P139014 | 7233SAO1 w/2% XL | 24.93 | 1.547 | 9.32 |
| 5.8 | R & D 1102 | S66246 | P139014 | 7233SAO1 w/2% XL | 24.93 | 1.547 | 9.32 |
| 5.8 | R & D 1102 | S66246 | P139014 | 7233SAO1 w/2% XL | 24.93 | 1.547 | 9.32 |
| 5.8 | R & D 1102 | S66246 | P139014 | 7233SAO1 w/2% XL | 24.93 | 1.547 | 9.32 |
| 5.8 | R & D 1102 | S66246 | P139014 | 7233SAO1 w/2% XL | 23.226 | 1.488 | 8.371 |
| 5.8 | R & D 1102 | S66246 | P139014 | 7233SAO1 w/2% XL | 20.757 | 1.604 | 6.963 |
| 5.8 | R & D 1102 | S66246 | P139014 | 7233SAO1 w/2% XL | 20.75 | 0.951 | 6.84 |
| 5.8 | R & D 1102 | S66246 | P139014 | 7233SAO1 w/2% XL | 19.3 | 0.86 | 5.645 |
| 5.8 | R & D 1102 | S88246 | P139014 | 7233SAO1 w/2% XL | 16.612 | 0.876 | 3.792 |
| 5.8 | R & D 1138/ 41130 | S68541/ S5967 | P138892 | 10% PA12/86.5% 7233SAO1/3% XL | 33.929 | 1.75 | 15.984 |
| 5.8 | R & D 1138/ 41130 | S68541/ S5967 | P138892 | 10% PA12/86.5% 7233SAO1/3% XL | 25.412 | 2.583 | 9.424 |
| 5.8 | R & D 1138/ 41130 | S88541/ S5967 | P138892 | 10% PA12/86.5% 7233SAO/3% XL | 24.227 | 2.081 | 9.287 |
| 5.8 | R & D 1138/ 41130 | S88541/ S5967 | P138892 | 10% PA12/86.5% 7233SAO1/3% XL | 23.907 | 1.344 | 8.827 |
| 5.8 | R & D 1138/ 41130 | S68541/ S5967 | P138892 | 10% PA12/86.5% 7233SAO1/3% XL | 22.803 | 1.748 | 8.245 |
| 5.8 | R & D 1138/ 41130 | S88541/ S5967 | P138892 | 10% PA12/86.5% 7233SAO1/3% XL | 22.024 | 0.752 | 8.821 |
| 5.5 | 41130 | S59677 | P138180 | 7233SNO1 | | | |
| 5.5 | 41130 | S59877 | P138180 | 7233SNO1 | 19.581 | 0.735 | 12.358 |
| 5.5 | 41130 | S59677 | P138180 | 7233SNO1 | 18.986 | 0.494 | 12.095 |
| 5.5 | 41130 | S59677 | P138180 | 7233SNO1 | 17.168 | 0.996 | 10.328 |
| 5.5 | 41130 | S59677 | P138180 | 7233SNO1 | 15.888 | 0.918 | 9.156 |
| 5.5 | 41130 | S59677 | P138180 | 7233SNO1 | 14.582 | 0.473 | 7.658 |

TABLE 2-continued

| | | | | | | | |
|---|---|---|---|---|---|---|---|
| 5.5 | 41130 | S59677 | P138180 | 7233SNO1 | 13.545 | 0.762 | 6.279 |
| 5.5 | 41130 | S59677 | P138180 | 7233SNO1 | 12.192 | 0.662 | 5.581 |
| 6.2 | R & D 1137 | S68043 | P137426 | 7233SAO1 w/3% XL | 30.464 | 1.361 | 13.559 |
| 6.2 | R & D 1137 | S68043 | P137426 | 7233SAO1 w/3% XL | 25.773 | 1.341 | 8.577 |
| 6.2 | R & D 1137 | S68043 | P137426 | 7233SAO1 w/3% XL | 25.235 | 2.492 | 7.158 |
| 6.2 | R & D 1137 | S68043 | P137426 | 7233SAO1 w/3% XL | 24.405 | 1.355 | 6.753 |
| 6.2 | R & D 1138 | S68042 | P137432 | 7233SAO1 W/10% PA12 w/3% XL | 27.116 | 1.659 | 10.449 |
| 6.2 | R & D 1138 | S68042 | P137432 | 7233SAO1 W/10% PA12 w/3% XL | 26.495 | 1.809 | 6.753 |
| 6.2 | R & D 1138 | S68042 | P137432 | 7233SAO1 W/10% PA12 w/3% XL | 24.552 | 1.685 | 6.062 |
| 6.2 | R & D 1138 | S68042 | P137432 | 7233SAO1 W/10% PA12 w/3% XL | 23.852 | 1.925 | 5.382 |
| 6.2 | R & D 1138 | S66758/ S6804 | P137433 | 6333SNO1 + 7233SAO1 W/10% PA12 w/3% XL | 29.92 | 2.724 | 16.854 |
| 6.2 | R & D 1138 | S66758/ S6804 | P137433 | 6333SNO1 + 7233SAO1 W/10% PA12 w/3% XL | 25.198 | 2.647 | 9.614 |
| 6.2 | R & D 1138 | S66768/ S6804 | P137433 | 6333SNO1 + 7233SAO1 W/10% PA12 w/3% XL | 23.244 | 3.8206 | 9.315 |

| Parison French size (O.D.) | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|
| 5.5 | 0.459 | 4 | 0 | 6.00 | 0.0861 | 20.25 | 0.661 | 0.002 | 7.59 |
| 5.8 | 0.426 | | 0 | 6.00 | | | | | |
| 5 8 | 0.638 | 5 | 3 | 6.00 | 0.064 | 18.5 | 1.46 | 0.0025 | 7.27 |
| 5.8 | 0.738 | 7 | 5 | 6.00 | 0.098 | 18.15 | 1.13 | 0.0025 | 7.01 |
| 5.8 | 0.738 | 6 | 5 | 6.00 | 0.093 | 18.15 | 1.13 | 0.0025 | 7.03 |
| 5 8 | 0.738 | 6 | 5 | 6.00 | 0.096 | 19.07 | 0.807 | 0.0025 | 7.33 |
| 5.8 | 0.738 | 6.5 | 5 | 6.00 | 0.053 | 17.72 | 0.982 | 0.0025 | 6.66 |
| 5.8 | 0.738 | 6 | 5 | 6.00 | 0.063 | 18.79 | 1.18 | 0.0025 | 7.18 |
| 5.8 | 0.501 | 7 | 7 | 6.00 | 0.08 | 18.25 | 1.28 | 0.0025 | 6.9 |
| 5.8 | 0.625 | 8 | 15 | 6.00 | 0.052 | 17.4 | 1.69 | 0.0025 | 6.51 |
| 5.8 | 0.35 | 8 | 25 | 6.00 | 0.0497 | 15.53 | 2.33 | 0.0025 | 6.23 |
| 5.8 | 0.357 | | 50 | 6.00 | | | | | |
| 5.8 | 0.175 | | 100 | 6.00 | | | | | |
| 5.8 | 0.822 | | 0 | 6.00 | | | | | |
| 5.8 | 0.851 | | 3 | 6.00 | | | | | |
| 5.8 | 0.649 | | 5 | 6.00 | | | | | |
| 5.8 | 0.524 | | 7 | 6.00 | | | | | |
| 5.8 | 0.653 | | 15 | 6.00 | | | | | |
| 5.8 | 0.385 | | 25 | 6.00 | | | | | |
| 5.5 | | | 0 | 6.00 | 0.197 | 15.4 | 0.45 | 0.002 | 8.7 |
| 5.5 | 0.719 | | 5 | 6.00 | 0.24 | 13.1 | 0.74 | 0.002 | 8.3 |
| 5.5 | 0.478 | | 15 | 6.00 | 0.24 | 12 | 0.03 | 0.002 | 8.5 |
| 5.5 | 0.926 | | 25 | 6.00 | | | | | |
| 5.5 | 0.483 | | 40 | 6.00 | | | | | |
| 5.5 | 0.207 | | 50 | 6.00 | 0.173 | 10.3 | 0.6 | 0.002 | 7.42 |
| 5.5 | 0.5 | | 70 | 6.00 | | | | | |
| 5.5 | 0.216 | | 100 | 6.00 | 0.12 | 11.1 | 0.005 | 0.002 | 6.97 |
| 6.2 | 0.595 | | 0 | 6.00 | | | | | |
| 6.2 | 0.414 | | 3 | 6.00 | | | | | |
| 6.2 | 0.835 | | 5 | 6.00 | | | | | |
| 6.2 | 0.409 | | 6 | 6.00 | | | | | |
| 6.2 | 0.656 | | 0 | 6.00 | | | | | |
| 6.2 | 0.504 | | 3 | 6.00 | | | | | |
| 6.2 | 0.491 | | 5 | 6.00 | | | | | |
| 6.2 | 0.625 | | 6 | 6.00 | | | | | |
| 6.2 | 1.265 | | 0 | 6.00 | | | | | |
| 6.2 | 1.177 | | 3 | 6.00 | | | | | |
| 6.2 | 1.444 | | 5 | 6.00 | | | | | |

TABLE 3

| Parison French size (O.D.) | Material Desc. | Vendor Mat'l. Lot # | Lot # | Mat'l. Formulation | Avg. Tensile (lb.) | Std. Dev | Elongation | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|---|---|---|---|---|---|---|
| 6.2 | R & D 1138 | S66758/ S6804 | P137433 | 6333SNO1 + 7233SAO1 W/10% PA12 w/3% XL | 25.933 | 3.108 | 9.646 | 0.9182 | 6 | | 6.00 | | | | | |
| 6.2 | R & D 1138 | S66758/ S6804 | P137433 | 6333SNO1 + 7233SA01 W/10% PA12 w/3% XL | 25.597 | 3.0238 | 9.189 | 1.239 | 7 | | 6.00 | | | | | |
| 6.2 | R & D 1138 | S66758/ S6804 | P137433 | 6333SNO1 + 7233SAO1 W/10% PA12 w/3% XL | 25.664 | 1.554 | 10.01 | 0.616 | 8 | | 6.00 | | | | | |
| 6.9 | R & D 1138 | S68541 | P138860 | 7233SAO1 W/10% PA12 w/3% XL | 32.284 | 2.73 | 12.779 | 1.27 | 0 | | 6.00 | | | | | |
| 6.9 | R & D 1138 | S68541 | P138860 | 7233SAO1 W/10% PA12 w/3% XL | 28.813 | 2.874 | 7.325 | 0.833 | 3 | | 6.00 | | | | | |
| 6.9 | R & D 1138 | S68541 | P138860 | 7233SAO1 W/10% PA12 w/3% XL | 27.19 | 1.399 | 6.899 | 0.38 | 5 | | 6.00 | | | | | |
| 6.9 | R & D 1138 | S68541 | P138860 | 7233SAO1 W/10% PA12 w/3% XL | 28.04 | 1.707 | 6.813 | 0.441 | 7 | | 6.00 | | | | | |
| 6.9 | R & D 1138 | S68541 | P138860 | 7233SAO1 W/10% PA12 w/3% XL | 26.263 | 2.33 | 5.918 | 0.599 | 15 | | 6.00 | | | | | |
| 7.6 | R & D 1138 | S68541 | P138885 | 7233SAO1 W/10% PA12 w/3% XL | 33.75 | 3.593 | 11.861 | 1.253 | 0 | | 10.00 | | | | | |
| 7.6 | R & D 1138 | S68541 | P138885 | 7233SAO1 W/10% PA12 w/3% XL | 31.242 | 1.784 | 6.799 | 0.4 | 3 | | 10.00 | | | | | |
| 7.6 | R & D 1138 | S68541 | P138885 | 7233SAO1 W/10% PA12 w/3% XL | 30.434 | 2.437 | 6.198 | 0.554 | 5 | | 10.00 | | | | | |
| 7.6 | R & D 1138 | S68541 | P138885 | 7233SAO1 W/10% PA12 w/3% XL | 28.015 | 0.95 | 6.141 | 0.24 | 7 | | 10.00 | | | | | |
| 7.6 | R & D 1138 | S68541 | P138885 | 7233SAO1 W/10% PA12 w/3% XL | 26.751 | 1.417 | 5.087 | 0.337 | 15 | | 10.00 | | | | | |
| 7.6 | R & D 1138 | S68541 | P138885 | 7233SAO1 W/10% PA12 w/3% XL | 25.218 | 1.368 | 4.385 | 0.408 | 25 | | 10.00 | | | | | |
| 8.5 | R & D 1138 | S88541 | P138886 | 7233SAO1 W/10% PA12 w/3% XL | 49.668 | 2.033 | 14.768 | 0.673 | 0 | | 12.00 | | | | | |
| 8.5 | R & D 1138 | S68541 | P138866 | 7233SAO1 W/10% PA12 w/3% XL | 36.825 | 2.034 | 6.604 | 0.348 | 5 | | 12.00 | | | | | |
| 8.5 | R & D 1138 | S68541 | P138886 | 7233SAO1 W/10% PA12 w/3% XL | 37.511 | 2.643 | 6.744 | 0.598 | 7 | | 12.00 | | | | | |

TABLE 3-continued

| Parison French size (O.D.) | Material Desc. | Vendor Mat'l. Lot # | Lot # | Mat'l. Formulation | Avg. Tensile (lb.) | Std. Dev | Elongation | Std. Dev | Nominal Pressure (atm) | Mrad | Nominal Balloon Diameter (mm) | Compliance (mm/atm) | Avg. Burst (atm) | Std Dev (atm) | Double Wall (ln) | Mean Burst Diameter (mm) |
|---|---|---|---|---|---|---|---|---|---|---|---|---|---|---|---|---|
| 8.5 | R & D 1138 | S68541 | P138886 | 7233SAO1 W/10% PA12 w/3% XL | 33.328 | 1.486 | 6.209 | 0.536 | | 15 | 12.00 | | | | | |
| 8.5 | R & D 1138 | S68541 | P138886 | 7233SAO1 W/10% PA12 w/3% XL | 31.665 | 0.813 | 5.576 | 0.244 | | 25 | 12.00 | | | | | |
| 9.9 | R & D 1138 | S68541 | P138887 | 7233SAO1 W/10% PA12 w/3% XL | 67 | 5.628 | 16.82 | 1.259 | | 0 | 12.00 | | | | | |
| 9.9 | R & D 1138 | S68541 | P138887 | 7233SAO1 W/10% PA12 w/3% XL | 52.887 | 2.465 | 8.570 | 0.642 | | 3 | 14.00 | | | | | |
| 9.9 | R & D 1138 | S68541 | P138887 | 7233SAO1 W/10% PA12 w/3% XL | 59.914 | 1.943 | 9.888 | 0.685 | | 5 | 14.00 | | | | | |
| 9.9 | R & D 1138 | S68541 | P138887 | 7233SAO1 W/10% PA12 w/3% XL | 63.975 | 4.47 | 10.121 | 0.734 | | 7 | 14.00 | | | | | |
| 9.9 | R & D 1138 | S68541 | P138887 | 7233SAO1 W/10% PA12 w/3% XL | 58.594 | 1.964 | 8.338 | 0.278 | | 15 | 14.00 | | | | | |
| 9.9 | R & D 1138 | S68541 | P138887 | 7233SAO1 W/10% PA12 w/3% XL | 51.635 | 1.417 | 6.892 | 0.321 | | 25 | 14.00 | | | | | |

TABLE 4

| Parison French size (O.D.) | Material Desc. | Vendor Mat'l. Lot # | Lot # | Mat'l. Formulation | (Mrad) | Nominal Balloon Diameter (mm) | Compliance mm/atm | Ave Burst (atm) | Std Dev (atm) | RBP (atm) | Double Wall (ln) | Mean Burst Diameter (mm) |
|---|---|---|---|---|---|---|---|---|---|---|---|---|
| 6.1 | R & D 1202 | S70350 | P139685 | 7233SAO1 w/⅛% XL | 0 | 6.00 | 0.178 | 17.68 | 0.459 | 15.29 | 0.0025 | 8.76 |
| 6.1 | R & D 1202 | S70350 | P139685 | 7233SAO1 w/⅛% XL | 0.5 | 6.00 | 0.194 | 17.08 | 0.22 | 15.93 | 0.0025 | 9.05 |
| 6.1 | R & D 1202 | S70350 | P139685 | 7233SAO1 w/⅛% XL | 1 | 6.00 | 0.168 | 16.98 | 0.025 | 18.85 | 0.0025 | 8.77 |
| 6.1 | R & D 1202 | S70350 | P139685 | 7233SAO1 w/⅛% XL | 2 | 6.00 | 0.167 | 16.37 | 0.483 | 13.86 | 0.0025 | 8.35 |
| 6.1 | R & D 1202 | S70350 | P139685 | 7233SAO1 w/⅛% XL | 3 | 6.00 | 0.174 | 16.96 | 0.081 | 16.54 | 0.0025 | 8.84 |
| 6.1 | R & D 1202 | S70350 | P139685 | 7233SAO1 w/⅛% XL | 5 | 6.00 | 0.17 | 16.13 | 0.303 | 14.55 | 0.0025 | 8.38 |
| 6.1 | R & D 1202 | S70350 | P139685 | 7233SAO1 W/⅛% XL | 7 | 6.00 | 0.146 | 15.91 | 0.297 | 14.37 | 0.0025 | 7.94 |
| AVERAGES | | | | | | | 0.1739 | 16.73 | 0.267 | 15.34 | 0.0025 | 8.58 |
| 6.1 | R & D 1203 | S70351 | P139687 | 7233SAO1 w/¼% XL | 0 | 6.00 | 0.198 | 17.24 | 0.603 | 14.1 | 0.0025 | 9.00 |
| 6.1 | R & D 1203 | S70351 | P139687 | 7233SAO1 w/¼% XL | 0.5 | 6.00 | 0.188 | 17.84 | 0.324 | 16.15 | 0.0025 | 8.9 |
| 6.1 | R & D 1203 | S70351 | P139667 | 7233SAO1 w/¼% XL | 1 | 6.00 | 0.18 | 17.59 | 0.45 | 15.24 | 0.0025 | 8.8 |
| 6.1 | R & D 1203 | S70351 | P139687 | 7233SAO1 w/¼% XL | 2 | 6.00 | 0.129 | 16.98 | 0.054 | 18.68 | 0.0025 | 7.78 |
| 6.1 | R & D 1203 | S70351 | P139687 | 7233SAO1 w/¼% XL | 3 | 6.00 | 0.131 | 16.98 | 0.037 | 16.77 | 0.0025 | 7.88 |
| 6.1 | R & D 1203 | S70351 | P139687 | 7233SAO1 w/¼% XL | 5 | 6.00 | 0.127 | 16.77 | 0.373 | 14.82 | 0.0025 | 7.8 |

TABLE 4-continued

| Parison French size (O.D.) | Material Desc. | Vendor Mat'l. Lot # | Lot # | Mat'l. Formulation | (Mrad) | Nominal Balloon Diameter (mm) | Compliance mm/atm | Ave Burst (atm) | Std Dev (atm) | RBP (atm) | Double Wall (ln) | Mean Burst Diameter (mm) |
|---|---|---|---|---|---|---|---|---|---|---|---|---|
| 6.1 | R &D 1203 | S70351 | P139687 | 7233SAO1 w/¼% XL | 7 | 6.00 | 0.117 | 16.11 | 0.147 | 15.37 | 0.0025 | 7.53 |
| AVERAGES | | | | | | | 0.1529 | 17.07 | 0.284 | 15.59 | 0.0025 | 8.21 |
| 6.1 | R & D 1137 | S70349 | P139688 | 7233SAO1 w/½% XL | 0 | 6.00 | 0.154 | 16.88 | 0.333 | 15.08 | 0.0025 | 8.20 |
| 6.1 | R & D 1137 | S70349 | P139686 | 7233SAO1 w/½% XL | 0.5 | 6.00 | 0.15 | 18.19 | 0.417 | 16.02 | 0.0025 | 9.07 |
| 6.1 | R & D 1137 | S70349 | P139668 | 7233SAO1 w/½% XL | 1 | 6.00 | 0.153 | 18.09 | 0.548 | 15.24 | 0.0025 | 8.2 |
| 6.1 | R & D 1137 | S70349 | P139688 | 7233SAO1 w/½% XL | 2 | 6.00 | 0.14 | 17.55 | 0.463 | 15.15 | 0.0025 | 8.06 |
| 6.1 | R & D 1137 | S70349 | P139688 | 7233SAO1 w/½% XL | 3 | 6.00 | 0.136 | 17 | 0.029 | 16.86 | 0.0025 | 8.06 |
| 6.1 | R & D 1137 | S70349 | P159688 | 7233SAO1 w/½% XL | 5 | 6.00 | 0.108 | 16.75 | 0.465 | 14.33 | 0.0025 | 7.43 |
| 6.1 | R & D 1137 | S70349 | P139688 | 7233SAO1 w/½% XL | 7 | 6.00 | 0.095 | 16.02 | 0.125 | 15.37 | 0.0025 | 7.16 |
| AVERAGES | | | | | | | 0.1337 | 17.21 | 0.34 | 15.44 | 0.0025 | 8.03 |
| 6.1 | R & D 1102 | S70348 | 139689 | 7233SAO1 w/1% XL | 0 | 6.00 | 0.168 | 16.98 | 0.465 | 14.56 | 0.0025 | 7.62 |
| 6.1 | R & D 1102 | S70348 | 139689 | 7233SAO1 w/1% XL | 0.5 | 6.00 | 0.107 | 18.12 | 0.308 | 16.51 | 0.0025 | 7.44 |
| 6.1 | R & D 1102 | S70348 | 139889 | 7Z33SAO1 w/1% XL | 1 | 6.00 | 0.113 | 18.04 | 0.448 | 15.71 | 0.0025 | 7.42 |
| 6.1 | R & D 1102 | S70348 | 139689 | 7233SAO1 w/1% XL | 2 | 6.00 | 0.108 | 17.95 | 0.305 | 16.36 | 0.0025 | 7.37 |
| 6.1 | R & D 1102 | S70348 | 139689 | 7233SAO1 w/1% XL | 3 | 6.00 | 0.11 | 17.94 | 0.298 | 16.38 | 0.0025 | 7.36 |
| 6.1 | R & D 1102 | S70348 | 139689 | 7233SAO1 w/1% XL | 5 | 6.00 | 0.098 | 17.64 | 0.479 | 15.15 | 0.0025 | 7.03 |
| 6.1 | R & D 1102 | S70348 | 139689 | 7233SAO1 w/1% XL | 7 | 6.00 | 0.081 | 17.11 | 0.602 | 13.98 | 0.0025 | 6.90 |
| AVERAGES | | | | | | | 0.112 | 17.68 | 0.415 | 15.52 | 0.0025 | 7.31 |

By way of non-limiting example, a particularly preferred process for forming a medical device balloon includes the following steps. First, a blend of PEBAX® 7233 and 1 percent by weight triallyl isocyanurate (as the additional cross-linking reactant) is extruded in the form of a tubing of desired diameter. The extruded tubing blend is then exposed to 3 megarads of irradiation via electron beam. The ends of the tubing are drawn or stretched to a reduced diameter, while a central portion between the ends of the tubing is left undrawn or unstretched, this central portion of the tubing being the portion from which the balloon 18 is blown. The tubing is then introduced into a mold and preliminarily heated to about 135° F. to about 150° F., then subjected to a blow pressure of about 350 psi to about 650 psi and a blow temperature of about 200° F. to about 250° F. The temperature of the mold is then raised by about 30° F. for about 30 sec to about 60 sec, to further set or cure the blown material. The mold is cooled and the blown material removed from the mold. The central, undrawn portion constitutes the balloon 18, and is cut from the tubing and mounted to the catheter shaft 11 in a suitable manner. The times, pressures and temperatures of this non-limiting example depend, of course, upon the thickness and inner diameter of the partially drawn tubing; those skilled in the art of medical balloon manufacture should be well capable of varying these conditions to yield a suitable balloon from any particular initial material blend.

Further Implementation of the Principles of the Disclosed Invention.

The principle of the present invention, that is, changing the durometer of only part of a suitably composed article by selectively exposing the article to cross-linking irradiation, can be applied to obtain a variety of useful medical devices. The article preferably comprises an irradiation cross-linkable mixture of a polyamide elastomer and at least one additional cross-linking reactant, and more preferably comprises one of the materials disclosed above. Many of the materials disclosed in International Applications WO 98/55161 and WO 98/15199, as well as in U.S. Pat. Nos. 5,900,444 (Zamore, May 4, 1999), No. 5,993,415 (O'Neil et al., Nov. 30, 1999) and No. 5,998,551 (O'Neil et al., Dec. 7, 1999) may also be useful for this purpose, depending upon whether the resulting medical device incorporating any particular material is in fact useful for its intended purpose. The entirety of all of these disclosures are expressly incorporated by reference herein. It is believed that those skilled in the art of catheter design and manufacture can readily determine the usefulness of the materials identified in these disclosures without undue experimentation, most readily by simple trial-and-error.

As indicated above, the material mixtures of the Examples were first formed into tubing 26 and irradiated before any balloon was blown from them. Accordingly, those mixtures of the Examples in Tables 1 through 4 which include the at least one additional cross-linking reactant constitute Examples of this further implementation of the present invention. The mixtures including nylon are probably particularly preferred in the practice of this further implementation of the present invention.

In any event, exposing only a part of an article to irradiation, or exposing different parts of an article to different amounts of irradiation, gives the different parts of the article different degrees of cross-linking, and therefore different durometers.

A wide range of medical devices having a varying durometer can be manufactured in accordance with the principles of the present invention. For example, while the present invention is useful in forming balloon, diagnostic and infusion catheters of a variety of diameters, the present invention is particularly useful in forming infusion catheters having an outside diameter below about 1 mm. Such catheters are sometimes known as "microcatheters" and are presently very popular products. They require a variety of functional characteristics. Microcatheters need to be strong enough to accommodate manipulation during introduction into and removal from a patient and to accommodate adequate pressure injection when deployed in a patient. At the same time, microcatheters need to have a low coefficient of friction (to allow the passage therein of micro-sized wire guides) and need to be small enough to allow their placement in small, distal vessels in the patient, yet still need to be soft enough to be able to flow directly into very tortuous paths within the patient.

Two known devices which meet these different needs are made from combinations of different materials in order to meet those needs. One known device is disclosed in U.S. Pat. No. 4,739,768 (Engelson, Apr. 26, 1988) and is believed marketed by Target Therapeutics (Los Angeles, Calif.) under the name "Tracker." The device disclosed in the Engelson patent comprises two or three small bore polyethylene tubes, each having a different hardness or durometer (hardest at the proximal end and softest at the distal end). The Engleson device also comprises an outer sleeve that extends the full length of the catheter and beyond the distal end of the distalmost inner tube. The outer sleeve ensures that the joints between the inner tubes of different durometer stay together during use of the device and, as desired for microcatheters, provides the device with a very soft and flexible distal tip. While the device achieves properties which have not previously been obtained with a catheter shaft composed of a single material, the device is unfortunately relatively complex.

Another known microcatheter which meets these different needs is marketed by Cook Incorporated (Bloomington, Ind.) under the trademark MicroFerret™. The Cook device comprises three separate polyethylene tubes of different durometer that are butt welded together to yield a catheter having varying degrees of stiffness along its length. The soft, flexible distal tip of the catheter resists kinking when advanced through tortuous vascular anatomy, yet the proximal rigid and medium shaft stiffnesses give the catheter high pushability, that is, the catheter is readily advanced within the patient. Unfortunately, the small diameters of the tubes make the butt bonds or welds difficult to form, and the finished product has relatively abrupt changes of stiffness along its length.

The drawbacks of the Engelson and Cook microcatheters arise, in part, because microcatheters generally require materials that have high moduli, that is, materials in which the initial slope of the applied force versus the resulting elongation of the materials is high. This property of high modulus is simply not possessed by conventional materials which are desirably soft. Thus, the prior devices have necessarily required a plurality of parts of different durometer in order to function well.

The present invention, however, provides a solution to this problem, since the amount of cross-linking along the catheter (and thus the durometer along the catheter) can be selected by varying the amount of irradiation to which the material of the catheter is exposed. The parts of the catheter that need to remain flexible or compliant are shielded by a metallic or other shield, while the parts which need to be stiffened are exposed to the irradiation source. The stiffness of the catheter can further be varied by forming the catheter via a "bump" extrusion process, wherein the wall thickness is increased in areas requiring more stiffness, and decreased in areas requiring more flexibility. The yield strength of the cross-linked material can be enhanced by stressing the material at an elevated temperature (longitudinally, circumferentially or both), even so far as the limits of the molecular bonds.

Such a catheter, and the method for forming it, are shown in FIG. 4. More particularly, in its simplest form a medical device 110 according to the present invention comprises a unitarily and continuously formed portion 108 having a varying durometer. The unitarily and continuously formed portion 108 preferably comprises at least a first unitarily and continuously formed part 102 and a second uniformly and continuously formed part 104, the first and second parts 102 and 104 having different durometers. The portion 108 preferably also comprises a transition zone 105 of continuously varying durometer connecting the first and second parts 102 and 104, the transition zone 105 being unitarily and continuously formed with the first and second parts 102 and 104 of the portion 108. In FIG. 4, the unitarily and continuously formed portion 108 is shown as a tubular portion 106. More particularly, the tubular portion 106 comprises and is configured as a catheter shaft 111. The first part 102 of the unitarily and continuously formed portion 108 constitutes a first (for example, a distal) catheter shaft segment 178 comprised in the catheter shaft 111, while the second part of the portion 108 constitutes a second (for example, a proximal) catheter shaft segment 180 comprised in the catheter shaft 111. The first and second catheter shaft segments 178 and 180 are unitarily and continuously formed with one another and have different durometers.

The first and second catheter shaft segments 178 and 180 are physically configured as desired, via molding, extrusion or other conventional processes. As shown, if the first catheter shaft segment 178 is shielded from a radiation source 200 by a tapered shield 196 while the second catheter shaft segment 180 is cross-linked by exposure to the radiation source, the first catheter shaft segment 178 will remain soft while the durometer of the second catheter shaft segment 180 is increased. The catheter shaft 111 is thereby given a varying durometer suitable for use in an infusion catheter, particularly in an infusion microcatheter having an outside diameter below about 1 mm. The resulting medical device 110 can include a radiopaque band (not shown) near its distal end, as an aid to positioning the device in a patient.

The transition zone 105 extends between the first and second catheter segments 178 and 180, and lies beneath the taper 202 of the tapered shield 196. The length of the taper 202 of the shield 196 establishes the length of the transition zone 105. Additional segments of different durometer and/or additional transition zones can be provided by simply including additional tapers on the shield 196. Alternatively, the additional segments or zones can be provided by moving the shield 196 with respect to the catheter shaft 111, and exposing the catheter shaft 111 to irradiation one or more additional times. The arrow 198 indicates the relative movement of the catheter shaft 111 and the shield 196 on the one hand, and the radiation source 200 on the other, during irradiation cross-linking.

If for some reason it is desired that the transition zone 105 be substantially eliminated, the taper 202 can be omitted from the shield 196 and a straight edge provided on the shield 196 in its place. Any transition between the first and second catheter shaft segments 178 and 180, or other unitarily and continuously formed first and second parts 102 and 104 of the portion 108, would then be limited to cross-linking resulting from diffraction of radiation passing the edge of the shield 196.

The exact opposite result can be readily achieved, that is, the durometer of the unitarily and continuously formed portion 108 can readily be varied continuously along the length of the portion 108. Such a result is the equivalent of having the transition zone 105 extend the entire longitudinal length of the portion 108 and could be obtained by employing a shield (not shown) whose taper 202 was as long as the portion 108 itself.

The catheter shaft 111 can be modified to make it useful for other purposes, for example, for use in a catheter needle set. Conventional catheter needle sets employ a catheter introduced into a patient directly on a needle. Such sets are typically used for introducing a short catheter into an abscess for drainage, for access to a bile duct or for other well-known purposes. In conventional sets, the tip of the catheter portion is made from a harder durometer material which is bonded to the distal end of a softer catheter shaft. A step or ledge is formed on the inside of the harder catheter tip portion near its distal end, and a ring or collar is provided on the needle which is capable of abutting or engaging the step or ledge. Such an arrangement prevents movement or slippage ("accordioning") of the catheter along the needle during passage of the catheter and needle through tissue of the patient. Particularly in smaller diameters, attachment of the harder catheter tip to the catheter shaft may be problematic.

The present invention solves this problem by permitting only a segment of the catheter shaft to be hardened. Thus, as shown in FIG. 5, one of the first and second catheter shaft segments 178 and 180 (for example, the first catheter shaft segment 178) can comprise a catheter tip 184. The other segment (for example, the second catheter shaft segment 180) then comprises a catheter body 186. Either the catheter tip 184 or the catheter body 186 can have the greater durometer. In the catheter needle set shown in FIG. 5, the catheter tip 184 has the greater durometer by having been exposed to a greater total fluence of irradiation than the catheter body 186. This could be achieved, for example, by disposing the shield 196 in a position opposite to that shown in FIG. 4, shielding the catheter body 186 while permitting the catheter tip 184 to be exposed to the radiation source 200. It should be recalled, however, that in other catheter structures it is often preferred that the catheter body 186 have a greater durometer than the catheter tip 184.

The catheter tip 184 is preferably configured for use in a catheter needle set. Accordingly, the catheter tip 184 includes a distal end 190, and a step or ledge 188 formed in the catheter tip 184 near its distal end 190. The medical device 110 then further comprises a needle 192 receivable in the catheter shaft 111 (in particular, in the catheter body 186). The needle 192 bears on it a ring, a collar, an enlargement or the like 194 which is engageable with or abuttable against the step or ledge 188 in the catheter tip 184. As in conventional catheter needle sets, such engagement or abutment prevents movement or slippage of the catheter shaft 111 with respect to the needle 192 during its passage through patient tissue. Advantageously, however, the resulting catheter 111 is of unitary, single piece construction, such that the problems of attaching a discrete tip to a catheter shaft are avoided.

Other modifications of the tubular portion 106 of the unitarily and continuously formed portion 108 can make the medical device 110 of the present invention useful for other purposes. For example, a variety of catheters are used for drainage of abscesses or other locations in a patient, for direct feeding of a patient into the patient's stomach (gastrostomy) or the like. Many of these catheters use an anchoring structure (such as a malecot, pigtail, loop or the like) to keep the catheter anchored in the stomach or cavity in which it is placed. Such catheters are considered indwelling, that is, they remain in the patient for an extended period of time. It is therefore important to patient comfort that such catheters be soft and pliable. Unfortunately, a stiffer, springier anchor is much more effective at keeping the catheter tip in place than the desired softer, more pliable one. The present invention solves this drawback by providing a medical device 110 in which the anchor structure of a catheter or the like has a relatively higher durometer than the balance of the catheter. The resulting device 110 has an anchor structure which is relatively stiff and springy, such that it is retained well in the patient, yet which is relatively soft and pliable along its shaft, thereby making it more comfortable for the patient.

Figure 6:
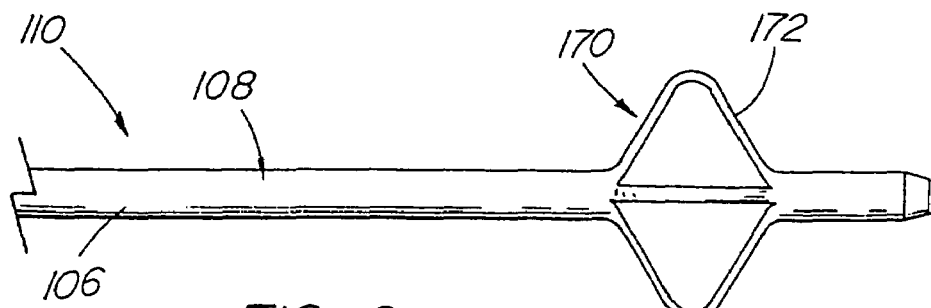
FIG. 6 is a side view of a portion of another preferred embodiment of the present invention.
Figure 7:
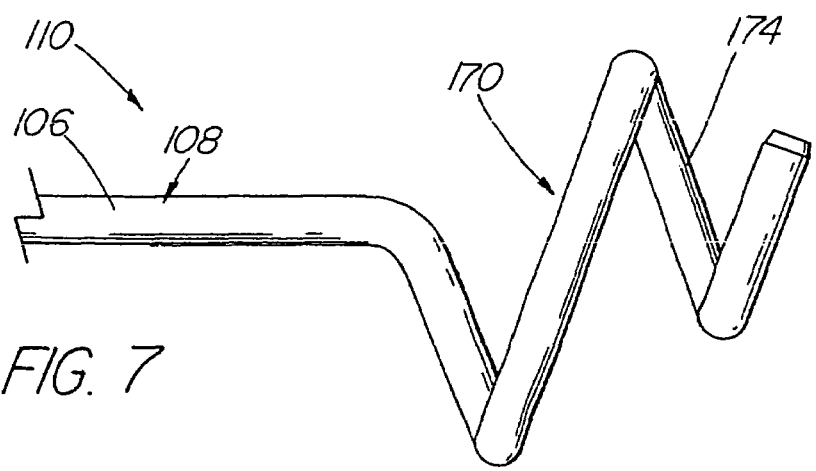
FIG. 7 is a side view of a portion of another preferred embodiment of the present invention.
Figure 8:
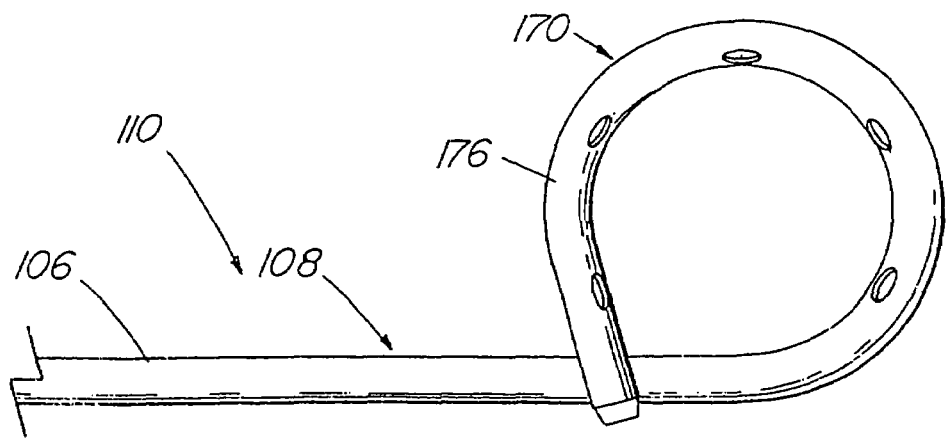
FIG. 8 is a side view of a portion of another preferred embodiment of the present invention.

Thus, as shown in FIGS. 6 through 8, the medical device 110 of the present invention can comprise a unitarily and continuously formed portion 108 which comprises a tubular portion 106 and an anchor structure 170 unitarily and continuously formed with the tubular portion 106, the anchor structure 170 and the tubular portion 106 having different durometers. Preferably, the durometer of the anchor structure 170 is greater than the durometer of the tubular portion 106. The anchor structure 170 can comprise a malecot 172 (FIG. 6), a pigtail 174 (FIG. 7), a loop 176 (FIG. 8) or the like.

Of course, the catheter tip 184 disclosed above may comprise the anchor structure 170, and in particular, any of the malecot 172, the pigtail 174 or the loop 176.

Any number of other unitarily and continuously formed parts of different durometer can be included in the portion 108 of the medical device 110 of the present invention. The specific shapes of such other parts would correspond to generally known shapes employed for generally known purposes, and the range of shapes need not be disclosed in detail here. Diagnostic catheters serve as specific examples of medical devices incorporating shapes adapted to patient anatomy. Some of the requirements for diagnostic catheters include the strength to resist rupture or burst during the high pressure injection of radiopaque dyes into patients, the ability to track well over a guide wire during introduction into a patient, a low coefficient of friction and thin-walled construction to allow the catheter to possess the largest possible lumen within the limits of the outside diameter of the catheter. Known materials for diagnostic catheters include polyethylene, polyamides, polyurethanes, polyvinylchloride and fluoropolymers. While each of these materials may have one property which lends itself well to use in diagnostic catheters, each also has other properties which results in a compromise when employed in diagnostic catheters.

More particularly, polyethylene is soft and flexible, but is not very strong. The softer, lower durometer grades of polyamides which are suitable for vascular catheters are also not very strong. Polyurethanes, in contrast, may be very strong, but they have a high coefficient of friction. Polyvinylchloride is flexible but has a low yield strength. Fluoropolymers such as PTFE and FEP have low coefficients of friction, but are very stiff. Moreover, most diagnostic catheters, as well as some therapeutic catheters, have curves or shapes at their distal ends which aid the placement of the catheters in the patient by complying with the anatomy in which they are being used. In general, softer materials which are typically suited to use in vascular catheters do not have good shape retention; they are not springy enough to be very effective.

Catheters formed from the cross-linkable mixtures of polyamide and cross-linking reactant disclosed herein overcome these drawbacks. They generally are flexible, strong and have low coefficients of friction, making them well suited for use in vascular catheters. Moreover, since particular areas where desired shapes may be formed can be selectively cross-linked and hardened, the catheters of the present invention should possess improved retention of such desired shapes, and therefore improved function.

Of course, the materials disclosed for use in the present invention can be used in combination with other materials to even greater functional advantage. As just one example, the materials of the present invention could be coextruded with a thin layer of TEFLON® or other lubricious material on its outside or inside diameter. This would add the property of vary low friction to a material that could be selectively stiffened or hardened anywhere within a medical device where it would be of advantage.

Figure 9:
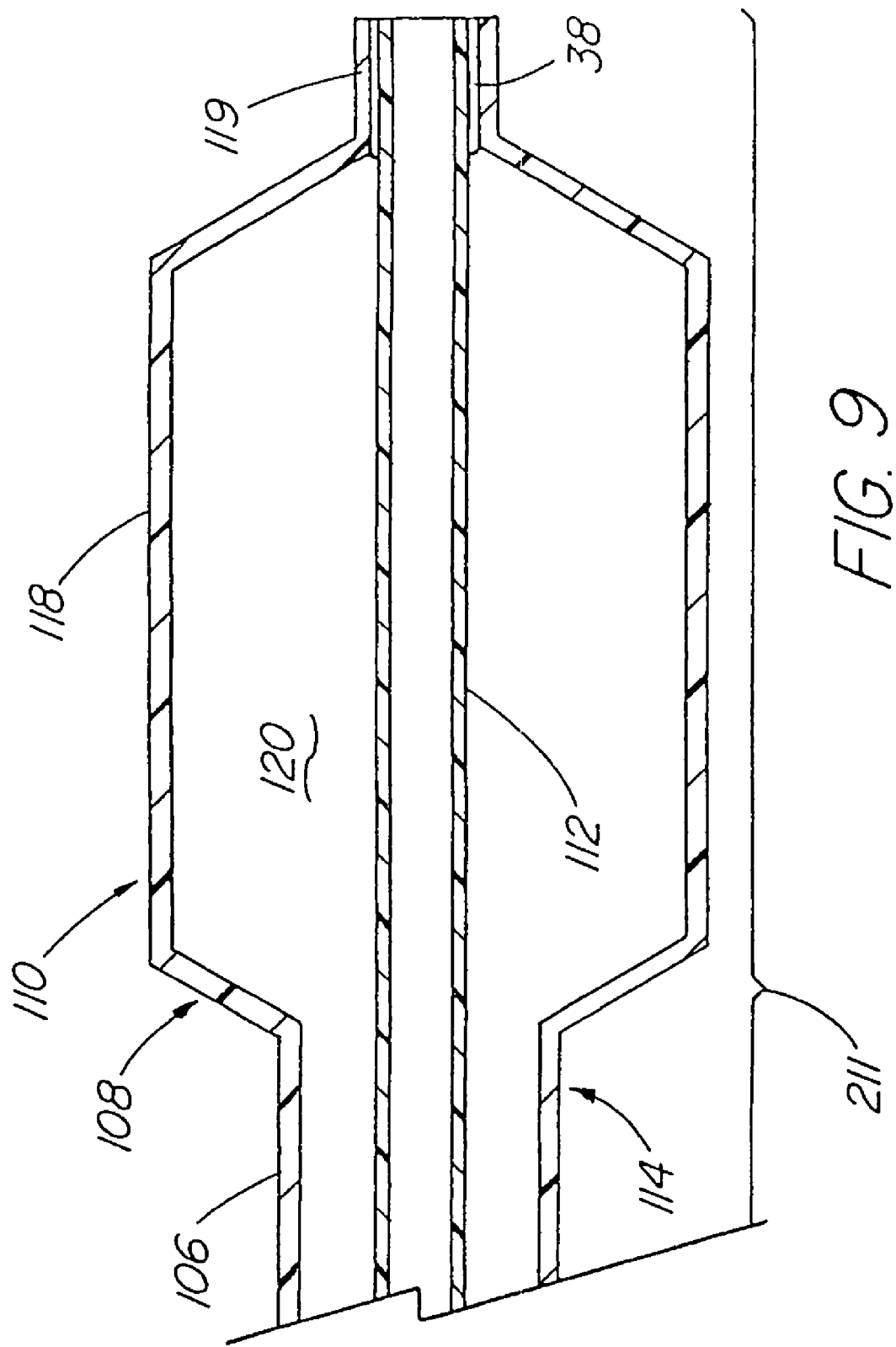
FIG. 9 is a cross-sectional view of another preferred embodiment of the present invention.

The principles of the present invention cart also be successfully applied to balloon catheters, and even more advantageously in balloon microcatheters having an outside diameter less than about 1 mm. In general terms, as shown in FIG. 9 the medical device 110 of the present invention can comprise a unitarily and continuously formed portion 108 of varying durometer, the portion 108 comprising a tubular portion 106 and an inflatable balloon 118 unitarily and continuously formed with the tubular portion 106, the balloon 118 and the tubular portion 106 having different durometers. More particularly, the medical device 110 of the present invention can first comprise a catheter shaft 211 having an outer catheter shaft 114 and an inner catheter shaft 112 received in the outer catheter shaft 114, wherein the outer catheter shaft 114 comprises the unitarily and continuously formed portion 108 (without regard to its particular configuration). Advantageously, the outer catheter shaft 114 of the medical device 110 comprises the tubular portion 106 of the portion 108. Preferably, the outer catheter shaft 114 further comprises the inflatable balloon 118, and is unitarily and continuously formed with it. The inflatable balloon 118 has a distal end 119 secured to and sealed to the inner catheter shaft 112, such that the space between the inner and outer catheter shafts 112 and 114 defines a lumen 120 for the delivery and removal of a pressurized inflation fluid to and from the inflatable balloon 118. The inner catheter shaft 112 can include a lumen formed therein (not shown) for receiving a guide wire therein.

The inflatable balloon 118 preferably has a durometer different from that of the outer catheter shaft 114 (or of the unitarily and continuously formed portion 108 or the tubular portion 106). More preferably, the inflatable balloon 118 comprises the preferred materials disclosed above for the discrete inflatable balloon 18. This is readily achieved by allowing the portion 108, whatever its shape or configuration (such as the tubular portion 106) to comprise an irradiation cross-linkable mixture of a polyamide elastomer and at least one additional cross-linking reactant. The portion 108 preferably comprises at least the first and second parts 102 and 104 described above, unitarily and continuously formed with one another, and at least one of the first and second parts 102 and 104 is exposed to cross-linking irradiation, such that they possess different durometers. The parts 102 and 104 can be exposed to different amounts of cross-linking irradiation, or only one of the parts 102 or 104 can be exposed to cross-linking irradiation while the other is shielded. In this particular embodiment, the balloon 118 is preferably formed from one of the parts 102 or 104, from the tubular part 106 or from the outer catheter shaft 114 by inflation after irradiation and cross-linking. Of course, a separate balloon like the balloon 18 described above can be connected to the outer and inner catheter shafts 114 and 112, and the durometer of one of them (for example, the outer catheter shaft 114) varied in the manner described herein.

When constructed from the preferred materials disclosed herein, the inflatable balloon 118 possesses many of the advantageous properties described above with respect to the inflatable balloon 18. Moreover, a medical device 110 having an inflatable balloon 118 unitarily and continuously formed with an outer catheter shaft 114 (or other element disclosed above) can readily be constructed in very small diameters, such as outside diameters below about 1 mm. The problems of precisely forming a fluid inlet/outlet hole through the side of a plural lumen catheter shaft (enabling inflation of a conventional separate balloon mounted on the exterior of the shaft) and securing a separate conventional balloon to such a shaft over such a hole are affirmatively avoided. The resulting medical device 110 possesses the outside diameter of a microcatheter and the superior balloon properties of the irradiation cross-linked materials, and is useful for performing angioplasty on very small vessels. In larger diameters, of course, the resulting medical device may be used to deploy a stent in the vascular system of a patient.

The particular process steps preferred for forming the medical device 110 of the present invention have been described above and need not be repeated in detail. In general, the process steps of the present invention comprise forming the elements disclosed above, irradiating those portions desired to have durometers different from the durometers of the portions not irradiated and assembling the elements into the medical device 110 described Similarly, the preferred materials which can be selectively cross-linked in part, by selective irradiation, and employed to construct the medical device 110 of the present invention, have been described in detail above. While such details need not be repeated, it should be remembered that it is particularly preferred that the processes by which the medical device 110 are assembled, are carried out with an irradiation cross-linkable mixture comprising a nylon block copolymer including polyether blocks separated by polyamide blocks, about 3 percent by weight triallyl isocyanurate and about 10 percent by weight nylons It is believed that the foregoing description clearly demonstrates that the medical device 110 of the present invention possesses significant advantages over prior medical devices. In particular, the present invention provides a medical device 110 which is particularly useful for deploying another medical device such as a stent into a patient or which is itself to be deployed into a patient, for example, for establishing a passage or lumen in a patient, for expanding a narrowed or obstructed passage or lumen in a patient or for introducing a therapeutic or diagnostic fluid into a patient. The medical device 110 of the present invention advantageously retains a plurality of functions performed in prior devices by discrete or separate elements while eliminating such discrete or separate elements. Moreover, the medical device 110 of the present invention can possess a continuous change in durometer, at least in part, so as to eliminate the locations for kinking or deformation present in prior devices having discrete or separate elements of different durometer.

The details of the construction or composition of the various elements of the medical devices 10 and 110 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, and particularly in the lower outside diameters, the medical devices 10 and 110 of the present invention should probably be considered to be single-use devices, rather than being reusable.

INDUSTRIAL APPLICABILITY

The present invention is useful for deploying another medical device such as a stent into a patient, or which is itself to be deployed into a patient, for example, for establishing a passage or lumen in a patient for expanding a narrowed or obstructed passage or lumen in a patient or for introducing a therapeutic or diagnostic fluid into a patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts and process steps.

The invention claimed is:

1. A process for assembling a medical device (110), the medical device (110) comprising a unitarily and continuously formed portion (108) having a varying durometer, and the process comprising:
    creating an irradiation cross-linkable mixture of a polyamide elastomer and at least one additional cross-linking reactant;
    forming the mixture into a unitarily and continuously formed portion (108),
    placing a shield (196) of varying density between the unitarily and continuously formed portion (108) and a source of cross-linking irradiation; and
    exposing the unitarily and continuously formed portion (108), at least in part, to cross-linking irradiation,
    wherein forming is carried out so as to yield a unitarily and continuously formed portion (108) comprising at least first and second parts (102 and 104) unitarily and continuously formed with one another, and the exposing step comprises exposing at least one of the first and second parts (102 or 104) to cross-linking irradiation,
    wherein the exposing step comprises exposing a unitarily and continuously formed transition zone (105) between the first and second parts (102 and 104) to a continuously varying amount of cross-linking irradiation.

2. A process for assembling a medical device (110), the medical device (110) comprising a unitarily and continuously formed portion (108) having a varying durometer, and the process comprising:
    creating an irradiation cross-linkable mixture of a polyamide elastomer and at least one additional cross-linking reactant;
    forming the mixture into a unitarily and continuously formed portion (108); and
    exposing the unitarily and continuously formed portion (108), at least in part, to cross-linking irradiation,
    placing a shield (198) between the unitary and continuously formed portion (108) and a source of cross-linking irradiation, prior to the exposing step, wherein the shield (196) has varying density between the unitarily and continuously formed portion (108) and the source of cross-linking irradiation.

3. A process for assembling a medical device (110), the medical device (110) comprising a unitarily and continuously formed portion (108) having a varying durometer, and the process comprising:
    creating an irradiation cross-linkable mixture of a polyamide elastomer and at least one additional cross-linking reactant;
    forming the mixture into a unitarily and continuously formed portion (108); and
    exposing the unitarily and continuously formed portion (108), at least in part, to cross-linking irradiation, the cross-linking reactant comprising
    an aromatic molecule containing at least two ring substituents, each of the ring substituents having labile hydrogens at a benzylic site therein, selected from the class consisting of 1,3,5 triethyl benzene: 1,2,4 triethyl benzene; and 1,3,5 triisopropyl benzene.

* * * * *

UNITED STATES PATENT AND TRADEMARK OFFICE
CERTIFICATE OF CORRECTION

PATENT NO. : 7,722,795 B2  
APPLICATION NO. : 10/813415  
DATED : May 25, 2010  
INVENTOR(S) : Scott E. Boatman et al.

Page 1 of 1

It is certified that error appears in the above-identified patent and that said Letters Patent is hereby corrected as shown below:

On the Title Page

In the left column, after item (62), under "Related U.S. Application Data", insert --which is a CIP of 09/663,747, filed September 15, 2000, now Pat. No. 6,592,550.--.

Signed and Sealed this
Third Day of May, 2011

David J. Kappos
*Director of the United States Patent and Trademark Office*